(12) United States Patent
Dörr et al.

(10) Patent No.: US 8,239,019 B2
(45) Date of Patent: Aug. 7, 2012

(54) IMPLANTABLE DEVICE FOR CARDIAC VECTOR DETERMINATION

(75) Inventors: Thomas Dörr, Berlin (DE); Andreas Kucher, Schwedt (DE); Jens Philipp, Berlin (DE); Ingo Weiss, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 1195 days.

(21) Appl. No.: 11/545,791

(22) Filed: Oct. 10, 2006

(65) Prior Publication Data
US 2007/0123940 A1  May 31, 2007

(30) Foreign Application Priority Data
Oct. 11, 2005 (DE) .......................... 10 2005 049 009

(51) Int. Cl.
*A61N 1/365* (2006.01)
(52) U.S. Cl. ......................... 607/9; 607/2; 607/4; 607/7
(58) Field of Classification Search .................... 607/2–9
See application file for complete search history.

(56) References Cited

U.S. PATENT DOCUMENTS
| 5,792,205 | A | 8/1998 | Alt et al. |
| 2005/0059897 | A1 | 3/2005 | Snell et al. |
| 2005/0090870 | A1 | 4/2005 | Hine et al. |
| 2005/0192505 | A1* | 9/2005 | Ostroff et al. .................. 600/509 |
| 2009/0076557 | A1* | 3/2009 | Zhang et al. ...................... 607/4 |

FOREIGN PATENT DOCUMENTS
EP  1 151 719  7/2001

OTHER PUBLICATIONS
German Search Report for priority application, dated Jul. 11, 2006.
European Search Report, dated Nov. 12, 2007.

* cited by examiner

*Primary Examiner* — Rex R Holmes
(74) *Attorney, Agent, or Firm* — ARC IP Law, PC; Joseph J. Mayo

(57) ABSTRACT

An implantable electrostimulation device having at least three input channels, (each forming a sensing channel), which are each connected to at least one electrode or to one terminal for an electrode, using which at least three different electrical potentials accompanying an excitation of cardiac tissue (myocardium) in a heart may be detected. Uses a signal processing unit which is connected to the input channels and is implemented to analyze the time curve of the potentials detected via the three sensing channels as three input signals in chronological relation to a periodically repeating trigger signal, which triggers a time window, and which is also implemented to detect predefined signal features for each of the three input signals within the time window triggered by the trigger signal, store them, and compare them to corresponding signal features of preceding time windows or of another input channel within the same time window.

31 Claims, 20 Drawing Sheets

IMPLANTABLE DEVICE FOR CARDIAC VECTOR DETERMINATION

This application takes priority from German Patent Application DE 10 2005 049 009.3 filed Oct. 11, 2005 the specification of which is hereby incorporated herein by reference.

BACKGROUND OF THE INVENTION

1. Field of the Invention

The present invention relates to an implantable electrostimulation device for a heart, in particular an implantable cardioverter/defibrillator.

2. Description of the Related Art

Implantable cardiac pacemakers and implantable cardioverters/defibrillators have reached a high level of development. The devices must operate reliably over years, since they are only accessible in the implanted state via an operation. This sets limits to the complexity of the devices. However, cardiac pacemakers and defibrillators are to be capable of detecting pathological states of the heart to be treated both with high sensitivity and also with high specificity, so that a state in need of treatment does not remain unrecognized and, in addition, unnecessary or incorrect treatment is avoided as much as possible. In connection with implantable cardioverters/defibrillators (ICDs), the difference between tachycardias which have their origin in the ventricle (ventricular tachycardias), and supraventricular tachycardias, which have their origin in the atrium, for example, is cited here.

Furthermore, the problems still exists of being able to recognize successful treatment as reliably as possible, in order to otherwise be able to adapt the treatment. In the simplest case, this relates to setting the strength of a stimulation pulse. This is to be dimensioned precisely so that the cardiac tissue (myocardium) of the stimulated heart chamber—i.e., atrium or ventricle—responds to the stimulation pulse and contracts as a result. However, stimulation pulses which are too strong are to be avoided in order to avoid unnecessary energy consumption, because the energy must be taken from a battery whose exhaustion makes an operation and replacement of the stimulation device necessary. Precisely in biventricular pacemakers for resynchronization therapy (CRT: cardiac resynchronization therapy), detecting the success of stimulation (capture detection) still causes problems, particularly in the left ventricle.

An array of individual solutions to the problems indicated here are known.

BRIEF SUMMARY OF THE INVENTION

The object of the present invention is to provide a cardiac stimulation device which has means which may expediently supplement or even replace the known means for solving the problems indicated.

This object is achieved according to the present invention by an implantable electrostimulation device which has at least three input channels, which are connected to at least one electrode or one terminal for an electrode, using which the at least three different electrical potentials accompanying excitation of the cardiac tissue (myocardium) in the heart may be detected. Each of the input channels forms a sensing channel. The electrostimulation device has a signal processing unit, which is connected to the three input or sensing channels and is implemented to analyze the time curve of the potentials detected via the three sensing channels as three input signals in chronological relation to a periodically repeating trigger signal. The trigger signal triggers a time window. Furthermore, the signal processing unit is implemented to detect signal features, which are predefined for each of the three input signals, within the time window triggered by the trigger signal, store them, and compare them to corresponding signal features of preceding time windows of the same sensing channel. Alternatively, the signal processing unit may also be implemented to compare signal features corresponding to one another of the input signals originating from different sensing channels within the same time window with one another.

The input or sensing channels may be connected to an electrode to be situated intracardially or to a neutral electrode, such as a pacemaker housing, as a counter electrode. The signals detected from the sensing channels are then unipolar signals.

However, it is preferable if each of the sensing channels is connected to two electrodes situated in the heart or in the periphery of the heart so that each of the sensing channels detects a bipolar input signal. For three bipolar sensing channels, at least three electrodes are required, each two of which are each connected to a sensing channel, without two sensing channels being connected to the same two electrodes. Two sensing channels thus always only share one of the two electrodes to which they are connected.

The present invention is based on the recognition that a type of electrocardiogram may be recorded using each of the three sensing channels, the three electrocardiograms obtained in this way differing, in particular in regard to the occurrence in relation to a shared reference instant of signal features corresponding to one another. By analyzing time shifts of this type, valuable additional information may be obtained about a current heart status, which may not be inferred from a single electrocardiogram. In particular, the analysis of the chronological relationship between signal features corresponding to one another in the different input channels allows improved tachycardia recognition, improved setting of the stimulation threshold value of a biventricular cardiac pacemaker, efficiency control of a biventricular cardiac pacemaker, and above all the recognition of ventricular fibrillations. If the three sensing channels each detect a far field of the myocardial potentials and a fourth sensing channel is provided for detecting a near field of the myocardial potentials, a ventricular fibrillation may be recognized in that the deflections of the three far field signals are very slight, while an excitation having a high rate may be recognized in the near field channel.

From the description above, it may be seen that the signal processing unit is preferably implemented to compare a detected current signal feature of an input signal in regard to the instant of the occurrence of a shape feature in the time window to the instant of the occurrence of a corresponding shape feature in another input signal or in a preceding time window. In regard to this aspect of the present invention and in regard to the entire present invention overall, a shape feature means a special signal feature which relates to the signal shape. In the simplest case, a shape feature is a signal peak. More complex shape features may be detected with the aid of a template approach. In general, a signal feature may be a shape feature, but it may also be a time feature in principle, for example.

An embodiment variation in which the signal processing unit is implemented to detect the occurrence of an amplitude maximum as a signal feature and the instant of its occurrence in the time window is especially preferred.

The trigger signal for triggering the time window may be an arbitrary, repeating trigger signal. For example, it may originate from a marker channel. More advantageously, however, the signal processing unit is implemented to derive the trigger signal from one of the input signals in such a way that the trigger signal is triggered by a signal feature of this input signal, such as the occurrence of an amplitude maximum. The occurrence of an amplitude maximum is a shape feature and thus also a signal feature of an input signal.

Furthermore, it is possible with the aid of a loop recorder for the input signals also to process time windows whose beginning is prior in time to the occurrence of the particular trigger signal. Moreover, the time window may be defined in relation to the trigger signal by specifying absolute time values, or by specifying relative time values which relate to the duration of a particular cardiac cycle.

The instant of the occurrence of the signal feature within the time window may also be detected in absolute time values in relation to the trigger signal, or by detecting the relative chronological position of the instant of the occurrence of the signal feature in the particular time window. The last case means that the instant of the occurrence of the signal feature is not detected in absolute time values, but rather in relation to the duration of the time window.

In relation to the trigger signal, it is advantageous if the trigger signal is derived from an input signal which represents a near field potential.

For the latter purpose, a fourth input channel is preferably provided as a fourth sensing channel, which is connected to at least one electrode or one terminal for an electrode, using which the near field of a fourth electrical potential accompanying the excitation of the cardiac tissue may be detected. The signal processing unit is implemented in these cases for the purpose of deriving the trigger signal from the input signal of the fourth sensing channel.

The first three sensing channels are preferably far field channels and are each connected to an electrode or a terminal for an electrode, using which a far field of an electrical potential accompanying an excitation of the cardiac tissue may be detected in the operating state of the implantable electrostimulation device.

In a preferred embodiment variation, the three input channels are connected to three electrode line terminals, namely a terminal for a proximal defibrillation electrode, such as an atrial shock electrode, a terminal for a distal defibrillation electrode, such as a ventricular shock electrode, and the housing of the implantable cardioverter/defibrillator, which is thus an active housing.

Preferably, at least one bipolar, right-ventricular electrode line, which has a ventricular ring electrode and a ventricular tip electrode, via which the near field is to be detected, is provided for detecting the input signal representing a near field via a near field channel.

Preferably, at least three input channels are far field channels, which are each connected to an electrode or to a terminal for an electrode, using which a far field of an electrical potential accompanying an excitation of the cardiac tissue (myocardium) is to be detected in the operating state of the implantable electrostimulation device, so that an input signal representing a particular far field is applied to the input channels. The implantable electrostimulation device has a signal processing unit which is connected to the input channels and is implemented to produce three differential signals differing from one another, which result from the difference of two signals applied to each input channel, and to calculate a particular maximum amplitude value for a particular cardiac cycle for each of the differential signals, which represents the maximum deflection of the particular differential signal within the particular cardiac cycle.

Instead of calculating the maximum amplitude value, the signal processing unit may be implemented to determine and analyze the amplitude (deflection) of each of the differential signals at a fixed reference instant within a cardiac cycle. However, the maximum amplitude value is the most informative and the simplest to determine. If necessary, the reference instant may be predefined by a marker channel known per se, which generates marker signals upon detecting a P wave, a T wave, or an R wave, for example.

In the special case, the differential signal is a signal which is to be represented as an electrocardiogram. In a special embodiment variation, the signal processing unit is therefore implemented to derive an electrogram from the input signals of each two input channels—i.e., preferably three electrocardiograms in total. Here, electrogram means an electrical signal which may be represented as an electrocardiogram. In this special case, the signal processing unit is implemented to determine one amplitude per cardiac cycle for each of the electrocardiograms. This amplitude is preferably the maximum deflection of the electrocardiogram, i.e., the maximum amplitude which occurs at the instant of a particular R wave. The R wave is a signal wave occurring as a result of the depolarization of the myocardium, which results in contraction of the particular cardiac muscle.

The present invention is based on the recognition that three maximum amplitudes obtained in this way have an information content which allows, for example, both differentiation of ventricular and supraventricular tachycardias and also reliable recognition of respective ventricular contractions.

In an embodiment variation which is especially preferred because of its simplicity, the signal processing unit is implemented to analyze the absolute value and sign of the maximum amplitude values in relation to one another. The three maximum amplitude values result in a 3-tuple, which is characteristic of the starting location of a ventricular excitation and thus allows right-side and also left-side ventricular contractions to be differentiated from one another and, in addition, a stimulated ventricular contraction to be differentiated from a natural ventricular contraction and finally a ventricular contraction of ventricular origin to be differentiated from a ventricular contraction of supraventricular origin. This is explained in greater detail in connection with the exemplary embodiments.

In addition to analysis of the 3-tuple, a template approach may also be used for comparing the maximum amplitude values. For this purpose, every detected maximum amplitude value is assigned to one of three categories, for example, namely small amplitude, moderate amplitude, or large amplitude. In this way, very compact descriptions of the maximum amplitude values to be compared to one another may be produced, which are also simple to analyze.

The present invention is based on the recognition that the particular amplitude of a particular differential signal may be understood as the absolute value of a vector, which may be added to the two other vectors to produce a summation vector, which particularly describes the direction of the excitation propagation in the myocardium at the particular instant. For this purpose, the angles between the three vectors forming the components of the summation vector are also to be considered. These angles are predefined by the spatial arrangement of the three electrodes connected to the three input channels in their implanted state. Since this spatial arrangement of the electrodes in implanted state remains essentially constant, the angles are constants, whose precise value is of subordinate significance if the information of interest may already be obtained by analyzing direction changes of the summation vector. The present invention makes use of this recognition, that essential information may be obtained solely by analyzing direction changes, and supplements it with the further recognition that in the simplest case only the absolute values of the amplitudes and their signs have to be analyzed in order to detect a direction change of the summation vector. For this purpose, it suffices to ascertain the particular amplitudes at a specific instant within the cardiac cycle, so that only three amplitude values are to be determined per cardiac cycle, namely one for each of the differential signals. A further recognition is that the most suitable reference instant is the instant of the occurrence of the R wave. This is suitable for two reasons: firstly, it is easy to identify, since it is inherent to every differential signal as the instant of the occurrence of the maximum amplitude. In addition, this instant identifies a particular ventricular contraction. Therefore, the origin location of the excitation may be concluded ideally from the direction of the summation vector at this instant. In turn, this allows—as already noted—stimulated ventricular excitations to be differentiated from natural ventricular excitations, left-ventricular excitations from right-ventricular excitations, and supraventricular excitations from ventricular excitations.

A further, more special advantage of the present invention is that it may be implemented with relatively little effort as a supplement to an implantable cardioverter/defibrillator known per se, by providing input channels for receiving the input signals, which are connected to electrodes required in any case, namely, in a preferred embodiment variation to a shock electrode in proximity to the atrium, to a ventricular shock electrode, and to an electrode formed by the housing of the implantable cardioverter/defibrillator. In a preferred embodiment variation, the atrial shock electrode is a relatively large-area, oblong proximal defibrillation electrode on an electrode line and the ventricular shock electrode is also an oblong distal defibrillation electrode on the same electrode line. This embodiment variation is connected to one input channel each, having a terminal for the atrial shock electrode and the ventricular shock electrode, while the third input channel is connected directly to the electrode formed by the active housing of the implantable cardioverter/defibrillator.

As will be explained in greater detail below, such an implantable cardioverter/defibrillator (ICD) is easy to design in such a way that it may differentiate ventricular tachycardias from supraventricular tachycardias, for example, with greater reliability than known devices.

If the implantable stimulation device is additionally implemented as a triple-chamber or multichamber pacemaker, which is capable as a biventricular pacemaker of stimulating both the right and also the left ventricle, the further advantage results that a multichamber pacemaker may easily thus be implemented as defined in the present invention so that it may differentiate the ventricular contractions because of right-ventricular or left-ventricular stimulation from one another and from natural ventricular contractions. This is particularly very advantageous in connection with the stimulation success control (capture control) explained at the beginning.

As already explained, to implement the present invention, it suffices to provide the implantable electrostimulation device—whether it is an implantable cardioverter/defibrillator or a multichamber cardiac pacemaker or a combination of the two—with a signal processing unit, which is to be connected in the above-mentioned way to electrodes and is implemented to analyze the absolute value and sign of the maximum amplitude values in relation to one another.

In a preferred embodiment variation, the electrostimulation device has a memory, in which an angle value is preferably stored permanently for each of the differential signals and/or each of the electrocardiograms, which allows, together with a particular amplitude of a particular electrocardiogram or the maximum amplitude value of the differential signal, a vector to be determined, which, upon vector addition with corresponding vectors which are derived from angles and amplitudes of the particular two other electrocardiograms or differential signals, produces a summation vector, whose direction is then to be analyzed by the signal processing unit. In the present case, the direction of the summation vector means the signed orientation of the vector, i.e., direction and also orientation of the summation vector.

The implantable electrostimulation device is preferably implemented for the purpose of ascertaining a possible direction change of the summation vector from cardiac cycle to cardiac cycle (beat to beat), i.e., to determine at least one amplitude value per cardiac cycle at the given reference instant for each of the electrocardiograms or differential signals. As already noted, it suffices to determine precisely one amplitude value for each electrocardiogram or differential signal per cardiac cycle, preferably at the instant of a ventricular contraction identified by a R wave, in order to implement the present invention in an especially simple and efficient way. In order to allow a change of the direction of the summation vector from cycle to cycle, the signal processing unit is preferably connected to a memory, in which the direction of the summation vector for the particular preceding cardiac cycle is to be stored. The signal processing unit is preferably implemented so that it only generates a signal identifying a direction change of the summation vector when the summation vector changes its direction by more than a predefined tolerance angle. It may be advantageous in this connection if the implantable stimulation device is implemented so that the directions of the summation vectors of multiple preceding cardiac cycles are to be stored.

In an especially preferred embodiment variation, the signal processing unit is implemented so that it may access predefined angle ranges, which are characteristic for specific excitation locations. In contrast to the preceding case, the signal processing unit does not only check whether the direction of the summation vector has changed in relation to the direction of the summation vector from the preceding cardiac cycle or the preceding cardiac cycles. Rather, the signal processing unit checks whether the particular ascertained direction of the summation vector falls into one of multiple angle ranges, one of these angle ranges being assigned to a stimulated right-ventricular ventricular contraction, for example, while another angle range is assigned to a stimulated left-ventricular ventricular contraction and a third angle range is assigned to a ventricular contraction because of natural stimulation conduction from the atrium to the ventricle. Further angle ranges may, for example, be assigned to the typical ectopic excitation foci for the ventricular stimulation.

In order to allow even more precise classification, particularly of tachycardias, or to determine a particular reference instant within a cardiac cycle as precisely as possible, the electrostimulation device preferably has a further input channel which is connected to an electrode or a terminal for an electrode, using which a near field of an electrical potential accompanying excitation of the cardiac tissue is to be detected in the operating state of the electrostimulation device, so that a signal representing the near field is applied to the further input channel. In this preferred case, the signal processing unit is also connected to the further input channel and is implemented to analyze the input signal representing the near field in each case in regard to signal peaks identifying a ventricular contraction.

In a preferred variation, in order to be able to use the particular heart rate to classify tachycardias, the signal processing unit is implemented in any case to analyze the chronological interval of the ascertained signal peaks and to derive the duration of a particular RR interval or a heart rate therefrom.

In addition, the signal processing unit may be implemented to derive a marker signal from a particular signal peak.

With appropriate implementation of the signal processing unit, this marker signal may be used to determine the amplitude (or deflection) of the differential signal or the electrocardiogram for each cardiac cycle at the instant predefined by the particular marker signal and to analyze the amplitudes thus obtained as absolute values of the components of a summation vector to determine the direction of the summation vector.

BRIEF DESCRIPTION OF THE DRAWINGS

The present invention will now be explained in greater detail on the basis of exemplary embodiments with reference to the figures. In the figures.

DETAILED DESCRIPTION

FIGS. 1 through 13 are used to explain the present invention in regard to implantable cardioverters/defibrillators (ICDs) in the form of single-chamber ICDs (FIGS. 1 and 2) and dual-chamber ICDs (FIGS. 3 through 8) and the analysis of the signal amplitudes obtained using these ICDs in regard to the classification of ventricular tachyarrhythmias (FIGS. 9 through 13).

The object of this analysis is to reduce a higher number of undesired ICD interventions, typical until now, because of supraventricular tachycardias (SVT).

Known single-chamber ICDs analyze ventricular interval changes (RR intervals) and use known onset and RR stability criteria for treatment inhibition solely in the case of sinus tachycardias and atrial fibrillations. Other known differentiation criteria are morphology criteria for differentiating between supraventricular and ventricular tachycardias.

In addition, atrial intervals are analyzed in known dual-chamber ICDs to improve the differentiation between ventricular tachycardias and supraventricular tachycardias.

The way in which the differentiation of various ventricular tachycardias may be improved using an implantable electrostimulation device according to the present invention will be explained in the following.

Figure 1:
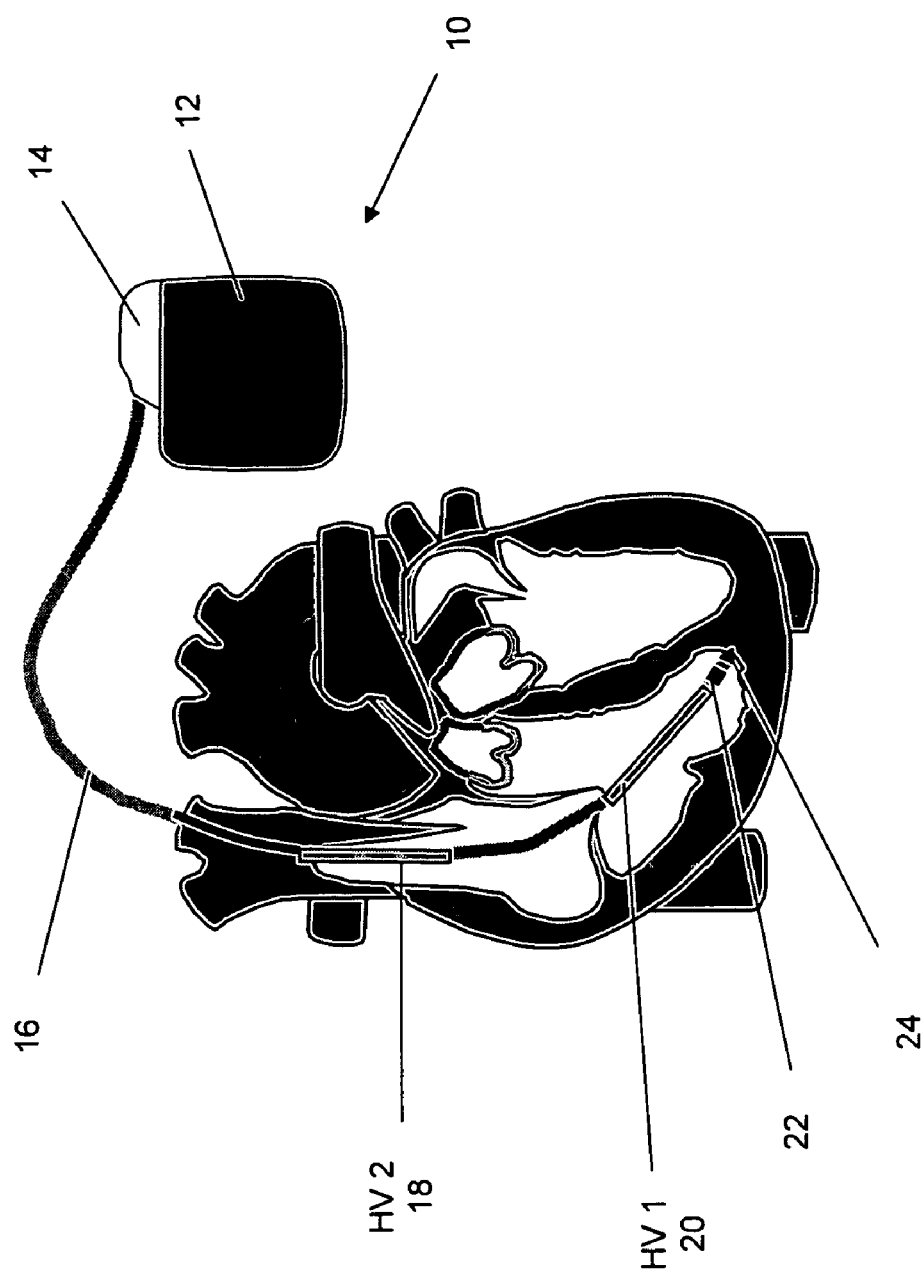
FIG. 1: shows the sketch of a single-chamber ICD according to the present invention having attached electrode lines and the position of the electrodes in the human heart.

FIG. 1 shows a suitable electrostimulation device in the form of a single-chamber ICD 10. The single-chamber ICD 10 has an active housing 12, i.e., a housing having an electrically conductive surface which forms an electrode.

An electrode line 16, which carries an oblong proximal shock electrode 18 and a distal shock electrode 20, also oblong, as well as a comparatively small-area ring electrode 22 and a tip electrode 24, also small-area, is connected to a header 14 of the ICD 10. The tip electrode 24 is located at the distal end of the electrode line 16.

The position of the electrodes in the implanted state is shown in FIG. 1. The proximal shock electrode 18 is located in the lower end of the vena cava superior in the area of the transition to the atrium in the implanted state. The distal shock electrode is located in the ventricle of a heart, the ventricular ring electrode 22 and the ventricular tip electrode 24 are situated in the area of the apex of the ventricle of the heart.

Figure 2:
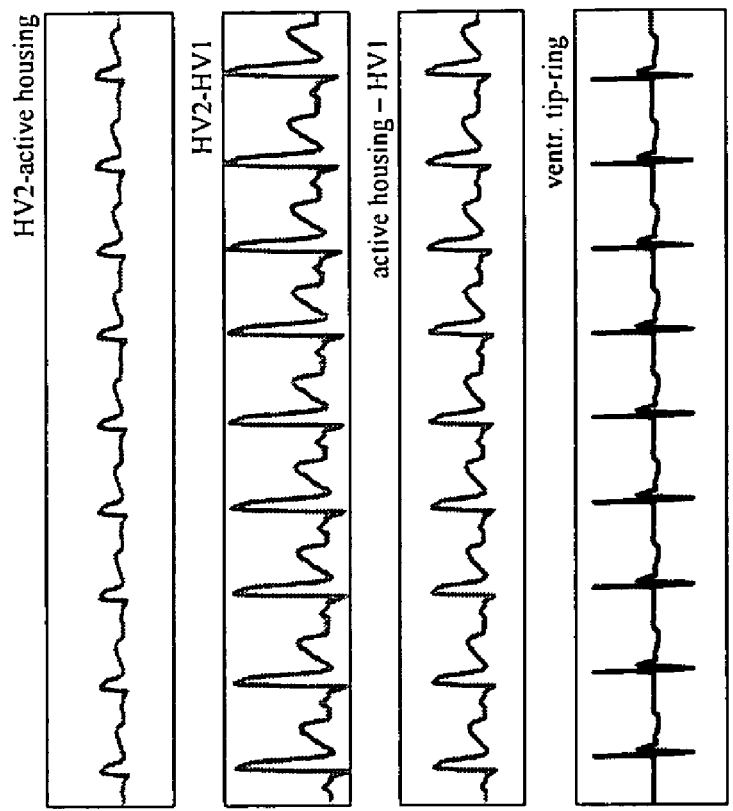
FIG. 2: shows electrocardiograms as they are to be detected using the constellation shown in FIG. 1, FIG. 3: shows a sketch, similar to FIG. 1, but in this case having a dual-chamber ICD.

Using the system shown in FIG. 1, the electrocardiograms shown in FIG. 2 may be obtained, each of which represents the curve of the potential difference between two electrodes as a differential signal, namely in FIG. 2a the differential signal which results as the difference of the potentials applied to the proximal shock electrode 18 and the active housing 12. FIG. 2b shows the differential signal which results from the curves of the electrical potentials applied to the two shock electrodes 18 and 20. FIG. 2c shows the differential signal which results from the potentials applied to the active housing 12 and the distal shock electrode 20.

The differential signals in FIGS. 2a through 2c each represent far field signals.

Finally, FIG. 2d shows the curve of the potential difference between the ventricular ring electrode 22 and the ventricular tip electrode 24. This differential signal is a near field signal.

While the three shock electrodes, namely the active housing 12, the proximal shock electrode 18, and the distal shock electrode 22, record differential signals which represent the far field of the ventricular excitation, a differential signal which represents the near field of the ventricular excitation is recorded via the electrode pair formed by the ventricular ring electrode 22 and the ventricular tip electrode 24. These differential signals are thus spiked signals which are especially suitable for the interval classification (i.e., the determination of the RR interval or the heart rate) and therefore are also already analyzed in known implantable stimulation devices.

The three differential signals recorded with the aid of the three shock electrodes, in contrast, represent the far field of the electrical potentials accompanying the ventricular contraction and are thus comparable to the signals which are obtained for a classical surface electrocardiogram with the aid of electrodes glued to the body. The three shock electrodes at least approximately form an equilateral triangle and thus correspond to the model presented according to Einthoven.

Figure 5:
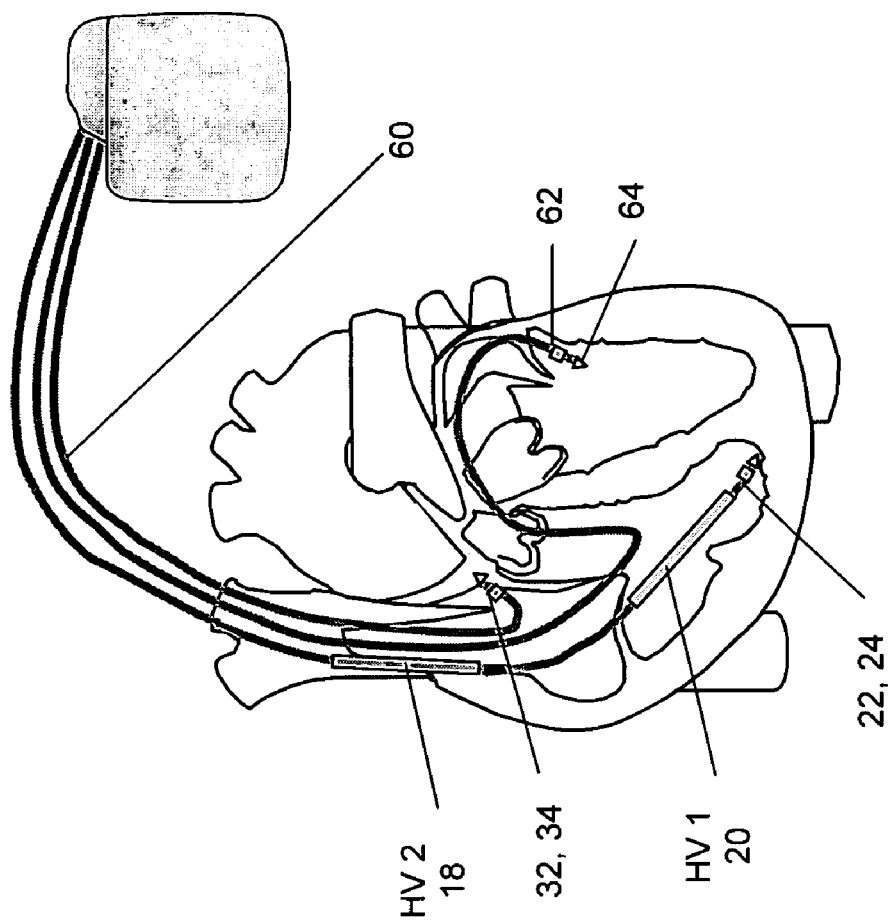
FIG. 5: shows a sketch of a triple-chamber ICD having attached, implanted electrodes.

FIG. 5 shows a triple-chamber ICD which, in addition to the electrodes already described with reference to FIGS. 1 and 3, has a third electrode line 60, which is guided as a left-ventricular electrode line via the coronary sinus and a lateral vein branching from the coronary sinus into the periphery of the left ventricle and which has a left-ventricular ring electrode 62 and a left-ventricular tip electrode 64 on its end.

Figure 6:
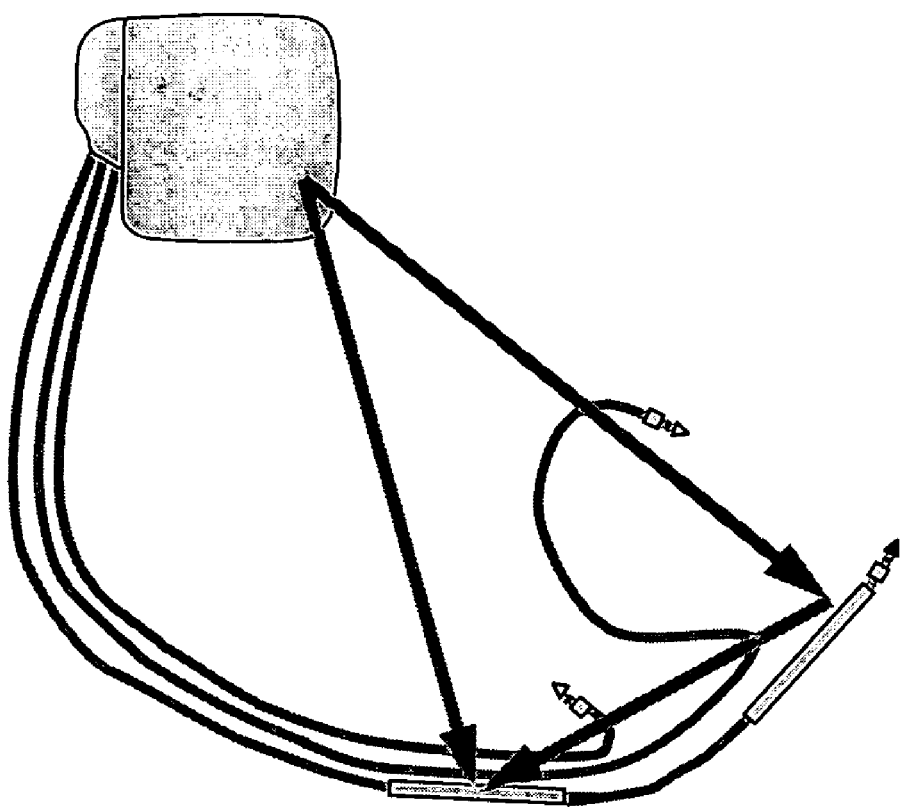
FIG. 6: shows an embodiment variation in which the input signals of the three far field channels are produced by analyzing the differential amplitudes, which are detected in pairs between an active housing of the triple-chamber ICD and a ventricular shock electrode, the ventricular shock electrode and an atrial shock electrode, and finally the active housing of the ICD and the atrial shock electrode.
Figure 7:
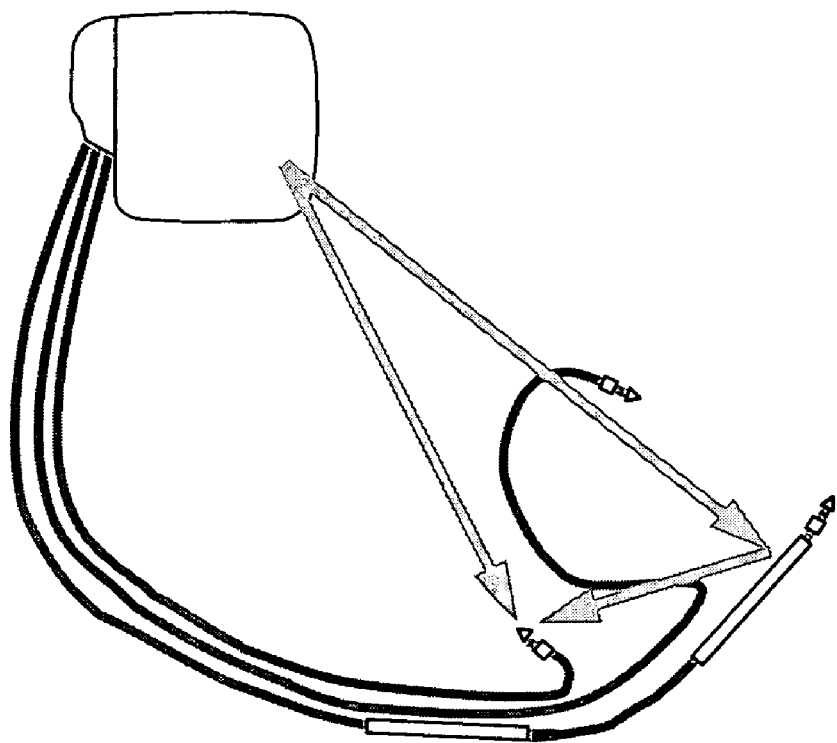
FIG. 7: shows an embodiment variation in which the input signals of the three far field channels are produced by analyzing the differential amplitudes, which are detected in pairs between an active housing of the triple-chamber ICD and a ventricular shock electrode, the ventricular shock electrode and an atrial ring or tip electrode, and finally the active housing of the ICD and the atrial ring or tip electrode.
Figure 8:
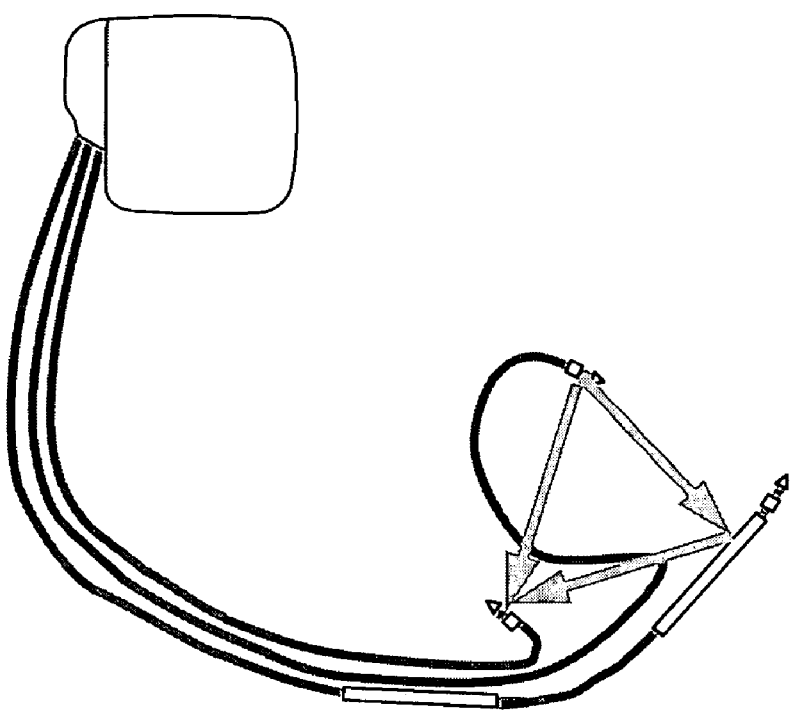
FIG. 8: shows an embodiment variation in which the input signals of the three far field channels are produced by analyzing the differential amplitudes which are detected in pairs between a left-ventricular ring or tip electrode and a ventricular shock electrode, the ventricular shock electrode and an atrial ring or tip electrode, and finally the left-ventricular ring or tip electrode and the atrial ring or tip electrode.

A triple-chamber ICD of the type shown in FIG. 5 allows the differential signals for the three far field channels to be ascertained in different ways, as shown in FIGS. 6, 7, and 8. The configuration in FIG. 6 has a result corresponding to those already explained with reference to FIGS. 1 and 2, while the configuration in FIG. 7 corresponds to the configuration which was already explained with reference to FIGS. 3 and 4. The configuration in FIG. 8 is similar to the configuration from FIGS. 3, 4, and 7, with the exception that the active housing of the ICD is not used as the third electrode, but rather the left-ventricular ring or tip electrode. Such a configuration, as shown in FIG. 8, will be explained once again in greater detail below with reference to FIGS. 14 and 15.

It will now be explained with reference to following FIGS. 9 through 13 how information about the origin location of a tachycardia, for example, may be obtained solely by analyzing the maximum amplitudes of the three differential signals (see FIGS. 2a through 2c and 4a through 4c). The known theory of Einthoven is used to explain this. The absolute values of the three maximum amplitudes may be understood as absolute values of vectors in the Einthoven triangle, which is known per se, which may be added vectorially and used to calculate a summation vector which reproduces the direction of the excitation propagation in the myocardium.

Figure 9:
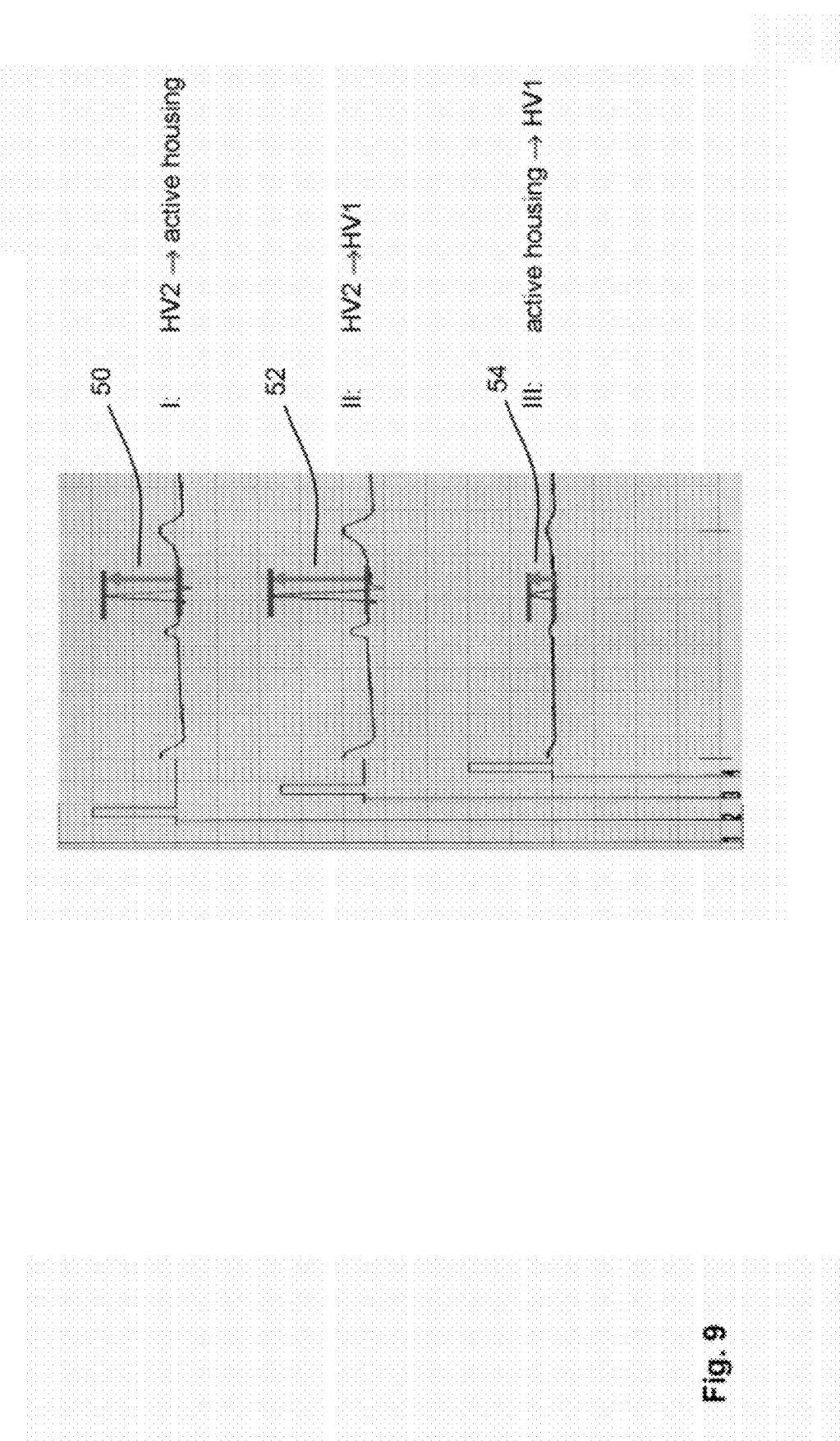
FIG. 9: shows a sketch to explain the determination of the maximum amplitudes in the particular electrocardiogram.
Figure 10:
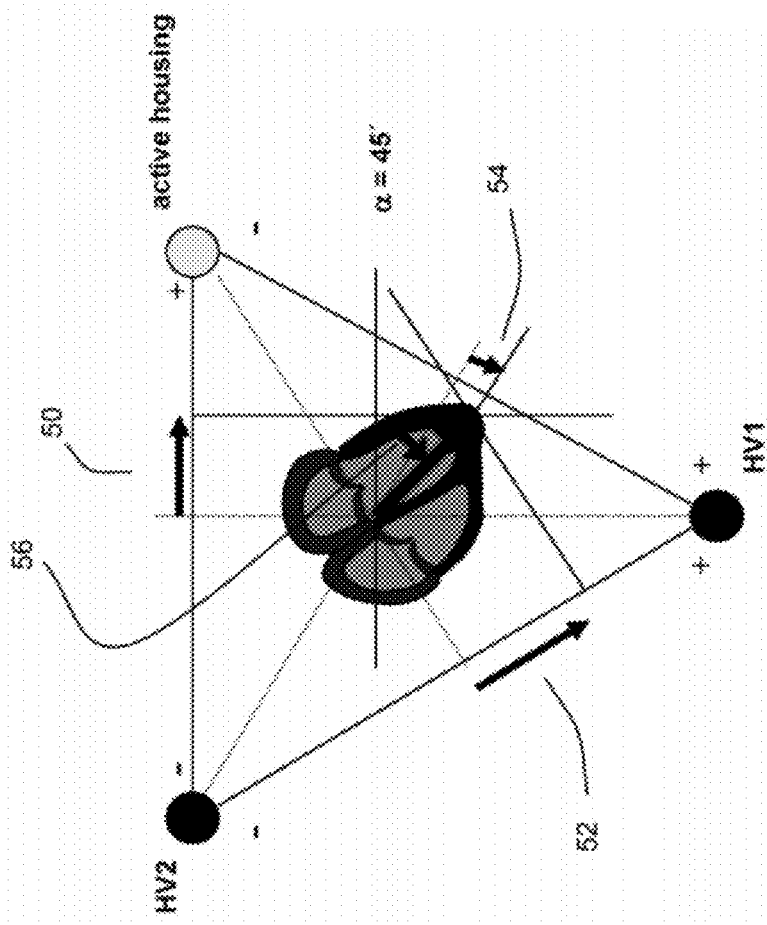
FIG. 10: shows a sketch to explain how a direction of the excitation propagation may be ascertained from the amplitude values ascertained as shown in FIG. 5.

First, FIG. 9 shows the determination of the maximum amplitude of a particular differential signal. The maximum amplitude occurs precisely once per cardiac cycle, at the instant of the R wave, i.e., at the instant of the contraction of the cardiac tissue as a result of the depolarization of the cardiac muscle cells. Therefore, three amplitude values are obtained per cardiac cycle from the three differential signals, which, as shown in FIG. 10, represent the absolute values of three vectors 50, 52, and 54, which may be added by vector addition to produce a summation vector 56. In principle, the consideration of the angles between the vector 50, 52, and 54 is required for the vector addition. These angles are predefined by the position of the three shock electrodes 12, 18, and 20 spanning a triangle. In an ideal equilateral triangle, each of the angles is 60°. As results from the following, knowing the precise sizes of the angles between the individual vectors 50, 52, and 54 is not absolutely necessary to nonetheless derive a sufficiently precise qualitative statement about the direction of the excitation propagation in the myocardium from the signs and absolute values of the three maximum amplitudes, which are to be derived from the differential signals recorded using the three shock electrodes 12, 18, and 20.

Figure 11:
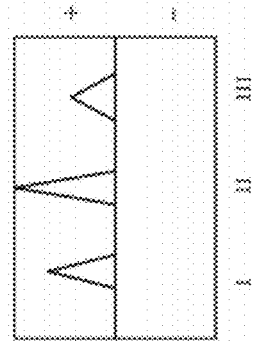
FIG. 11: shows a compact illustration of the amplitude values ascertained as shown in FIG. 5.

A compact illustration of the three maximum amplitudes is shown in FIG. 11. Expressed in numbers, the three absolute values and signs of the three maximum amplitudes may also be summarized in a 3-tuple, which represents the direction of the excitation propagation sufficiently precisely in each case.

FIGS. 9 through 11 show typical amplitudes during a natural excitation propagation from the atrium to the ventricle via the AV node of a heart.

Figure 12:
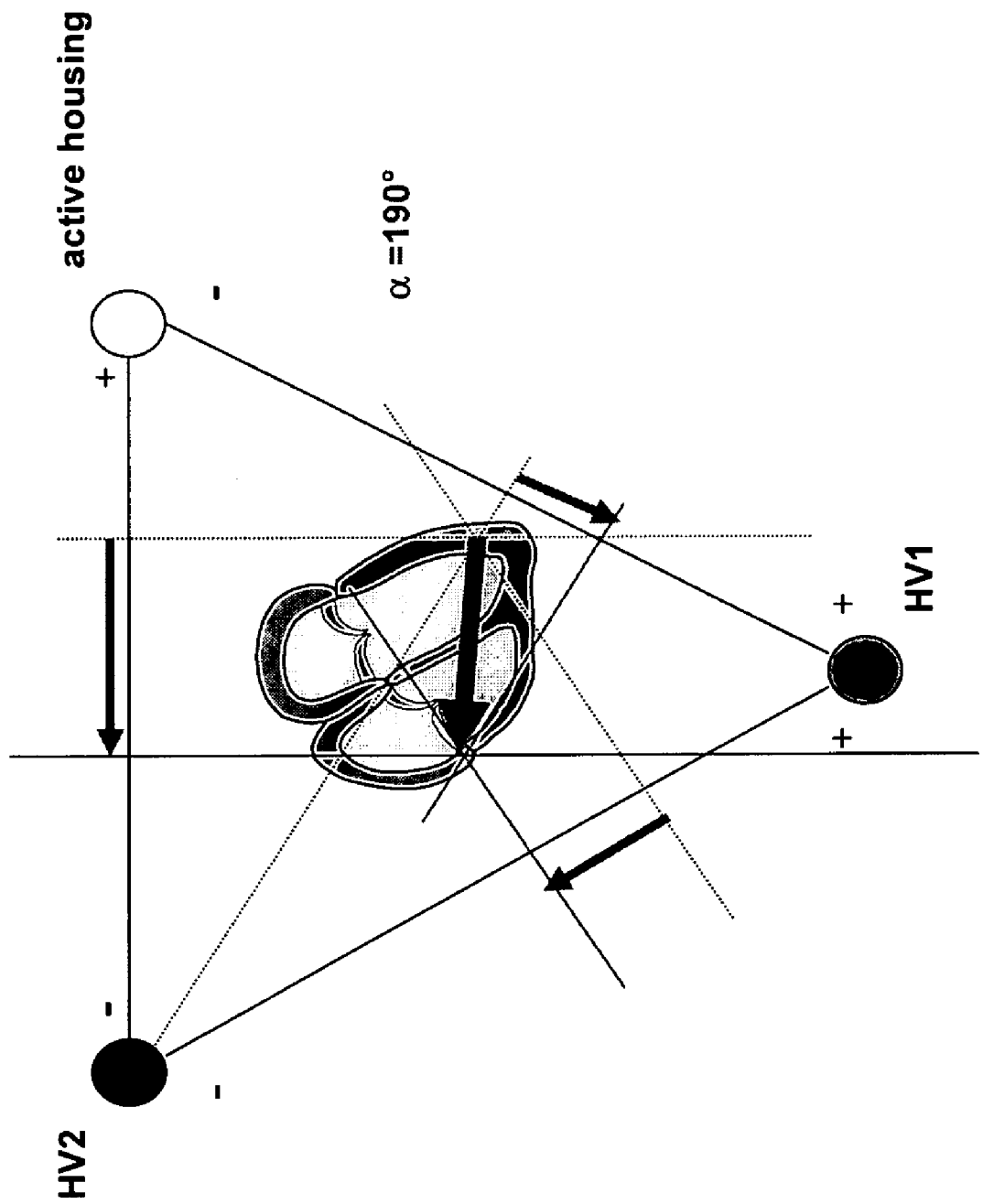
FIG. 12: shows a sketch, similar to FIG. 6, but for a case typical for a ventricular tachycardia.

FIG. 12 shows how strongly the three maximum amplitudes change when the ventricular excitation has its origin in an ectopic excitation focus in the right ventricle, as is the case during a ventricular tachycardia, for example. It may be seen how the direction of the summation vector (expressed by an angle a) has changed by 145°.

In the meaning of the angle definition for the angle a introduced with FIGS. 10 and 12, the summation vector in the normal sinus rhythm extends in a direction characterized by an angle a between 30° and 90°.

Since the propagation of the ventricular excitation also originates from the AV node in the case of supraventricular tachycardias (SVT), a is also between approximately 30° and 90° in the case of supraventricular tachycardias. This is particularly true for supraventricular tachycardias such as ventricular fibrillation, ventricular flutter, stable, atrial reentry tachycardia, AV node reentry tachycardia, or Wolf-Parkinson-White syndrome.

In the case of ventricular tachycardias, the origin location of the tachycardia is in the ventricle. Originating from an arrhythmogenic origin location, the excitation front propagates in the myocardium of the ventricle in an altered direction. This altered excitation propagation direction is reflected in a direction change of the summation vector. In turn, this direction change is reflected in an altered angle a (see FIG. 12). An angle change of this type occurs in a monomorphous ventricular tachycardia or in a polymorphous ventricular tachycardia independently of the frequency of the atrium.

In the case of a paroxysmal ventricular tachycardia, the direction of the summation vector change suddenly with occurrence (onset) of the tachycardia. A ventricular extrasystole also results in a direction change of the summation vector, precisely for a cardiac cycle in which the ventricular extrasystole occurs. In contrast, a sustained ventricular tachycardia produces a permanent change of the direction of the summation vector over many cardiac cycles. A stable ventricular reentry tachycardia having a 1:1 retrograde line (from the ventricle to the atrium) results in a change of the direction of the summation vector by approximately 180°.

However, a stimulated ventricular contraction (using a typical simulation electrode situated in the apex of the ventricle) also results in a similar direction of the summation vector. This is to be considered when determining a tachycardia and may simultaneously be used for stimulation success control (capture control), as will be described in the following.

In order to be able to classify tachycardias automatically as reliably as possible through the signal processing unit, in a preferred embodiment variation, the signal processing unit is implemented so that it may not only execute an analysis of the direction of the summation vector by analyzing the 3-tuple described, but rather additionally also considers known differentiation criteria.

Figure 3:
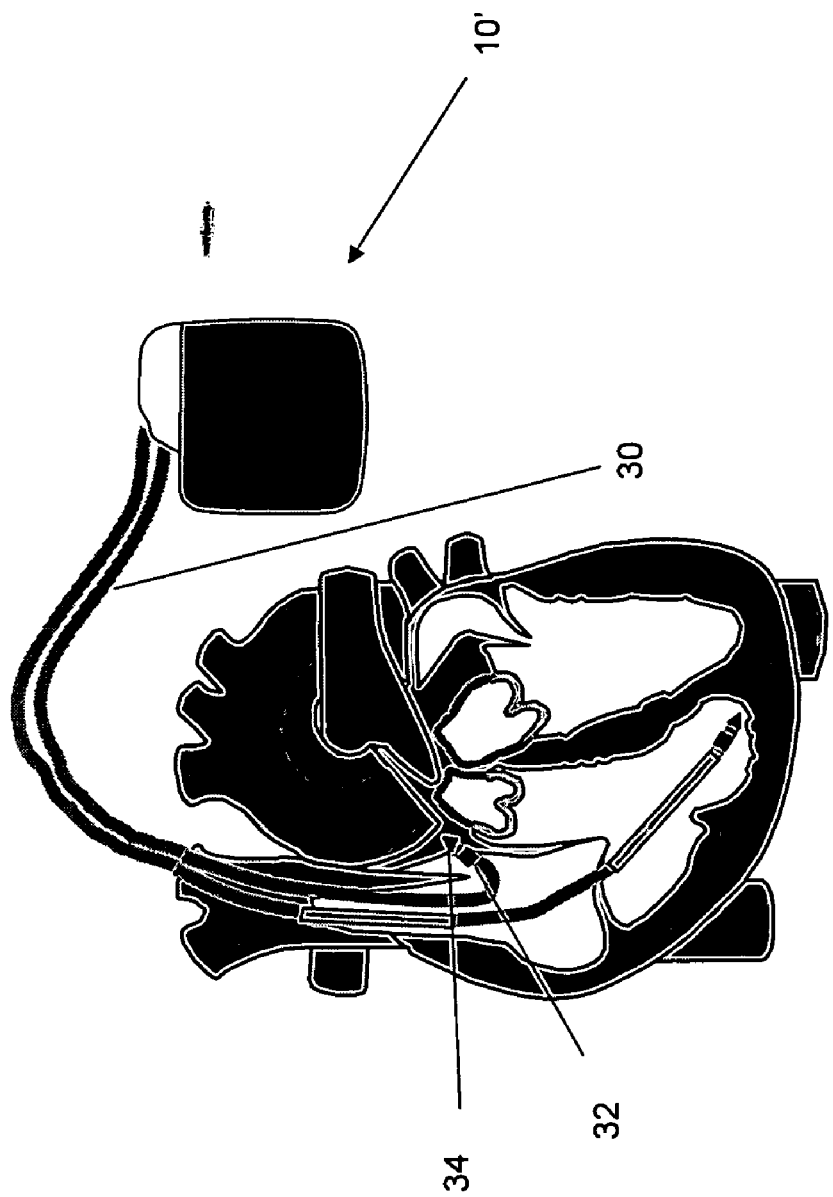
Figure 4:
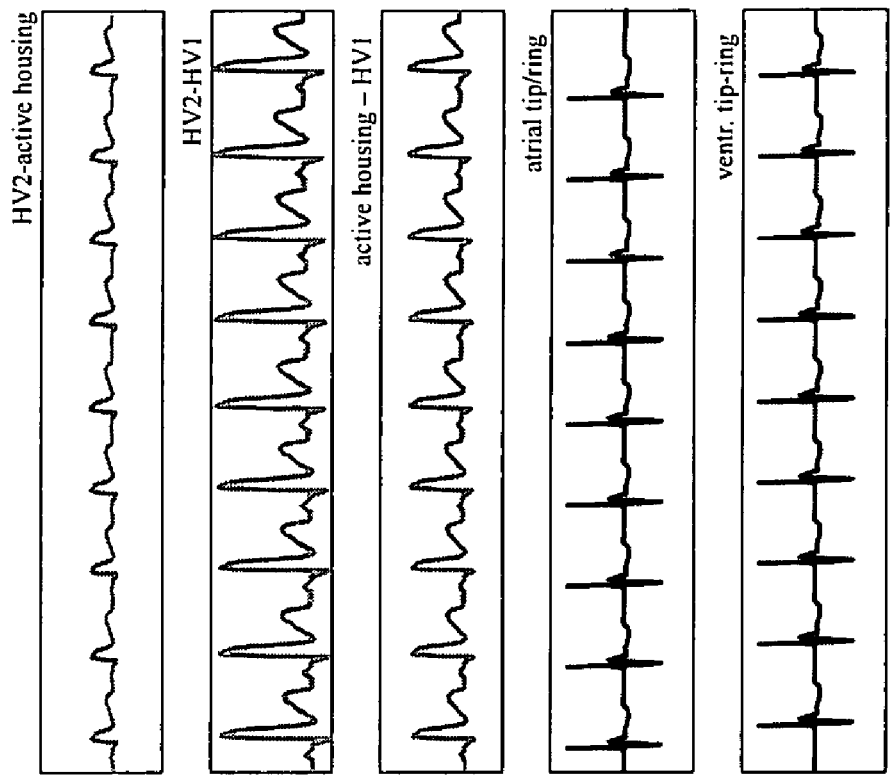
FIG. 4: shows electrocardiogram signals as they may be obtained using the dual-chamber ICD shown in FIG. 3.

For this purpose, it may be especially advantageous if the ICD is a dual-chamber ICD, as shown in FIG. 3. This dual-chamber ICD 10' is connected to a second electrode line 30, which is used for stimulating the atrium and which has an atrial ring electrode 32 and atrial tip electrode 34 on its distal end. In addition to the four differential signals already shown in FIG. 2, a fifth differential signal is to be obtained via these two atrial electrodes 32 and 34, which results from the potentials to be detected in the atrium and reflects their near field.

Figure 13:
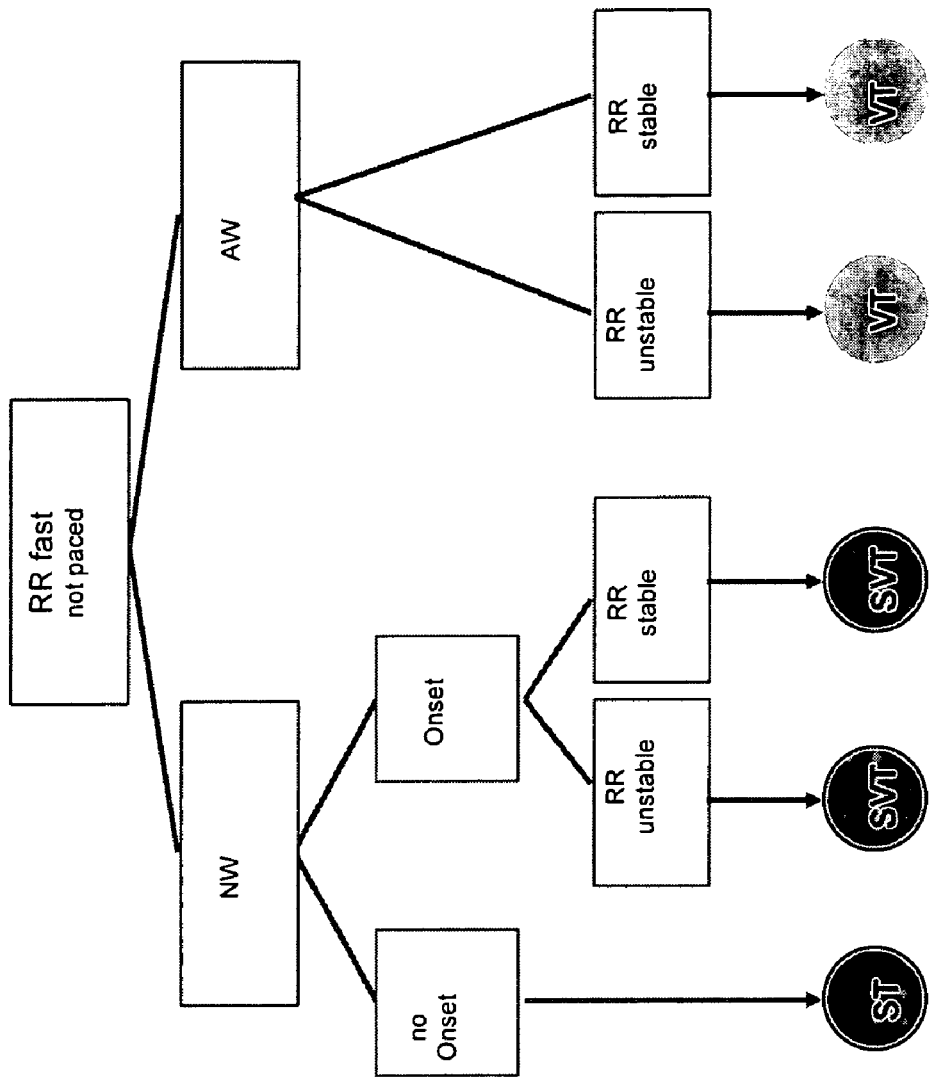
FIG. 13: shows a graphical illustration of a classification algorithm, as it is implemented by the signal processing unit of an implantable stimulation device according to the present invention.

FIG. 13 illustrates the mode of operation of a signal processing unit which considers both the direction of the summation vector and also rate criteria, as are to be obtained using electrode pairs such as the ventricular ring electrode 22 and the ventricular tip electrode 24 or the atrial ring electrode 32 and atrial ring electrode 34, to classify ventricular tachycardias.

As may be seen from FIG. 13, the starting point for a classification of the ventricular tachycardia is a high ventricular rate (RR rate). In this case, the signal processing unit first ascertains, by analyzing the 3-tuple described above, whether the direction of the excitation propagation (the summation vector does not first have to be calculated for this purpose—as explained above) is located in a normal angle range (NW) or in an abnormal angle range (AW).

If the signal processing unit ascertains that the direction of the excitation propagation in the ventricle is in an abnormal angle range (AW), the signal processing unit further checks whether the ventricular rate (RR rate) is stable or unstable. In both cases, a ventricular tachycardia is detected.

If the signal processing unit ascertains that the direction of the excitation propagation is in the normal angle range (NW), the signal processing unit checks further whether the ventricular rate (RR rating) has changed gradually (no onset) or has changed suddenly (onset). In a first case (no onset), the signal processing unit detects a sinus tachycardia.

In the second case (sudden occurrence of the tachycardia, onset), the signal processing unit checks whether the ventricular rate is unstable or stable. In both cases, the signal processing unit ascertains a supraventricular tachycardia (SVT).

The following abbreviations are used in FIG. 13:
NW normal angle range
AW abnormal angle range
ST sinus tachycardia
SVT supraventricular tachycardia
VT ventricular tachycardia As already indicated, the direction of the excitation propagation may also be expediently analyzed for stimulation success control. This is particularly advantageous in biventricular stimulation devices, i.e., for example, in triple-chamber ICDs.

Figure 14:
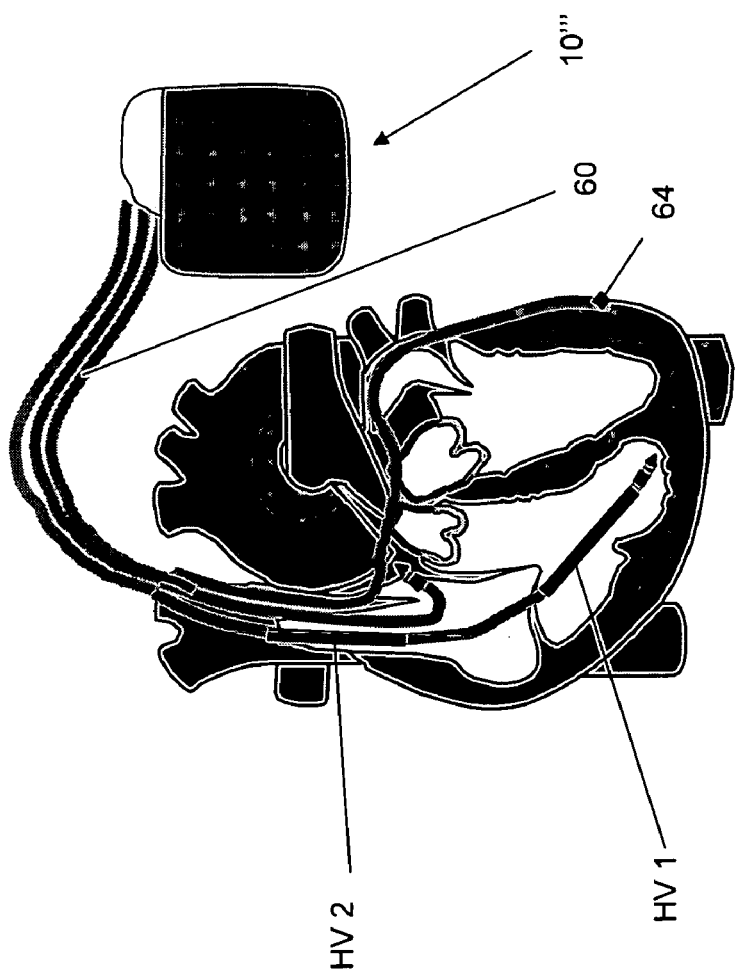
FIG. 14: shows a sketch, similar to FIG. 1, but in this case having a triple-chamber ICD.

Such a triple-chamber ICD is shown in FIG. 14. In contrast to the single-chamber and dual-chamber ICDs shown in FIGS. 1 and 2, the triple-chamber ICD 10''' from FIG. 14 is equipped with a third electrode line 60, which is used for stimulating the left ventricle and is typically inserted via the coronary sinus and a lateral vein branching from the coronary sinus. The left-ventricular electrode line 60 has a left-ventricular tip electrode 64 on its distal end.

Figure 15:
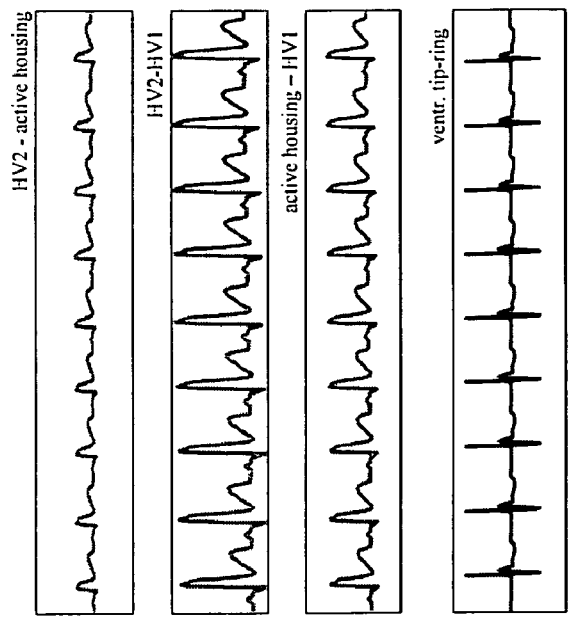
FIG. 15: shows electrocardiogram signals as they may be obtained using the triple-chamber ICD shown in FIG. 10.

The differential signals shown in FIG. 15, which are to be recorded using the triple-chamber ICD shown in FIG. 14, correspond to those which were already explained in connection with FIG. 2.

As already noted, it may be inferred from the direction of the excitation propagation whether a ventricular contraction may be attributed to a successful stimulation.

This is explained in greater detail with reference to FIG. 16. In a stimulated heart, the electrical excitation in the heart begins at the point of the stimulation electrode. From there, the excitation front propagates via the ventricle. This means that the excitation propagation and thus the direction of the summation vector is different than in a non-stimulated heart action, in which the excitation originates from the AV node.

In a biventricular stimulation of the heart, the excitation front will propagate in an altered direction, originating from the two stimulated origin locations. This changed excitation propagation direction is reflected in a different angle of the summation vector. During a successful biventricular stimulation, an angle results as shown in FIG. 16 and maximum amplitudes of the differential signals result as are shown in compact form in FIG. 17.

Figure 17:
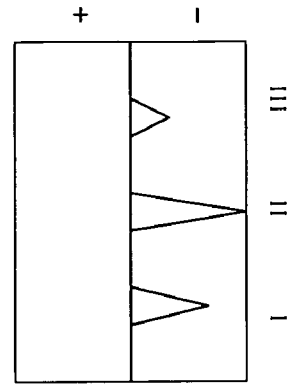
FIG. 17: shows a compact illustration of the amplitudes as they result in the case of a successful biventricular stimulation, similar to FIG. 7.

The illustration in FIG. 17 shows the polarity of the individual maximum amplitudes and their amplitude ratio to one another. Therein, I identifies the maximum amplitude of the differential signal which was obtained between the active housing 12 and the proximal shock electrode 18, II identifies the maximum amplitude of the differential signal which was recorded between the proximal shock electrode 18 and the distal shock electrode 20, and III identifies the maximum amplitude of the differential signal which was detected between the distal shock electrode 22 and the active housing 12.

Figure 16:
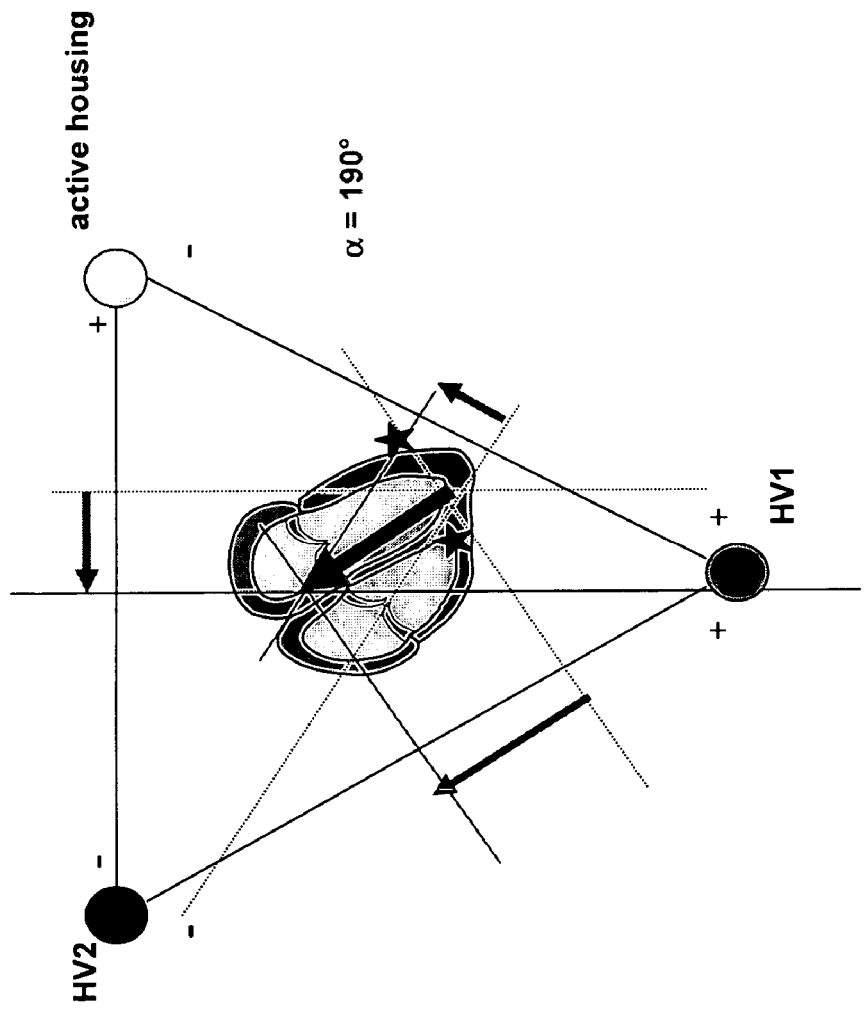
FIG. 16: shows a sketch, similar to FIG. 6, but for the case of successful biventricular stimulation here.
Figure 18:
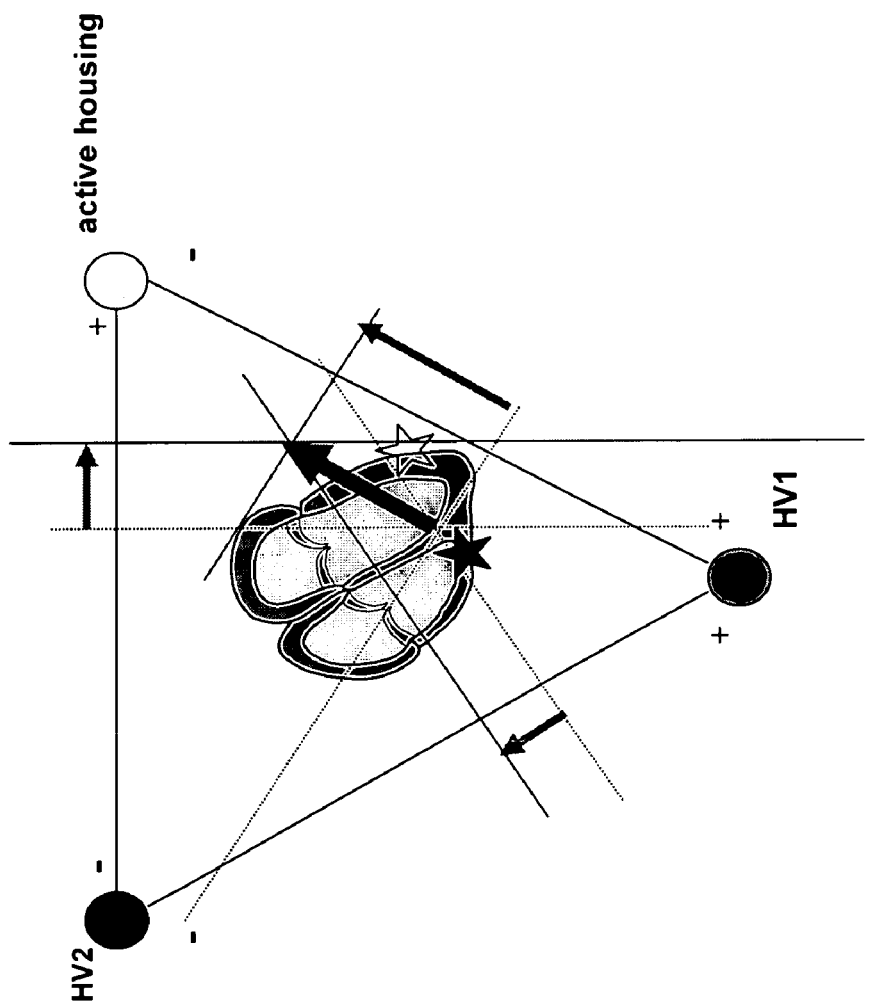
FIG. 18: shows a sketch, similar to FIG. 6, but for the case of successful right-ventricular stimulation but unsuccessful left-ventricular stimulation.
Figure 20:
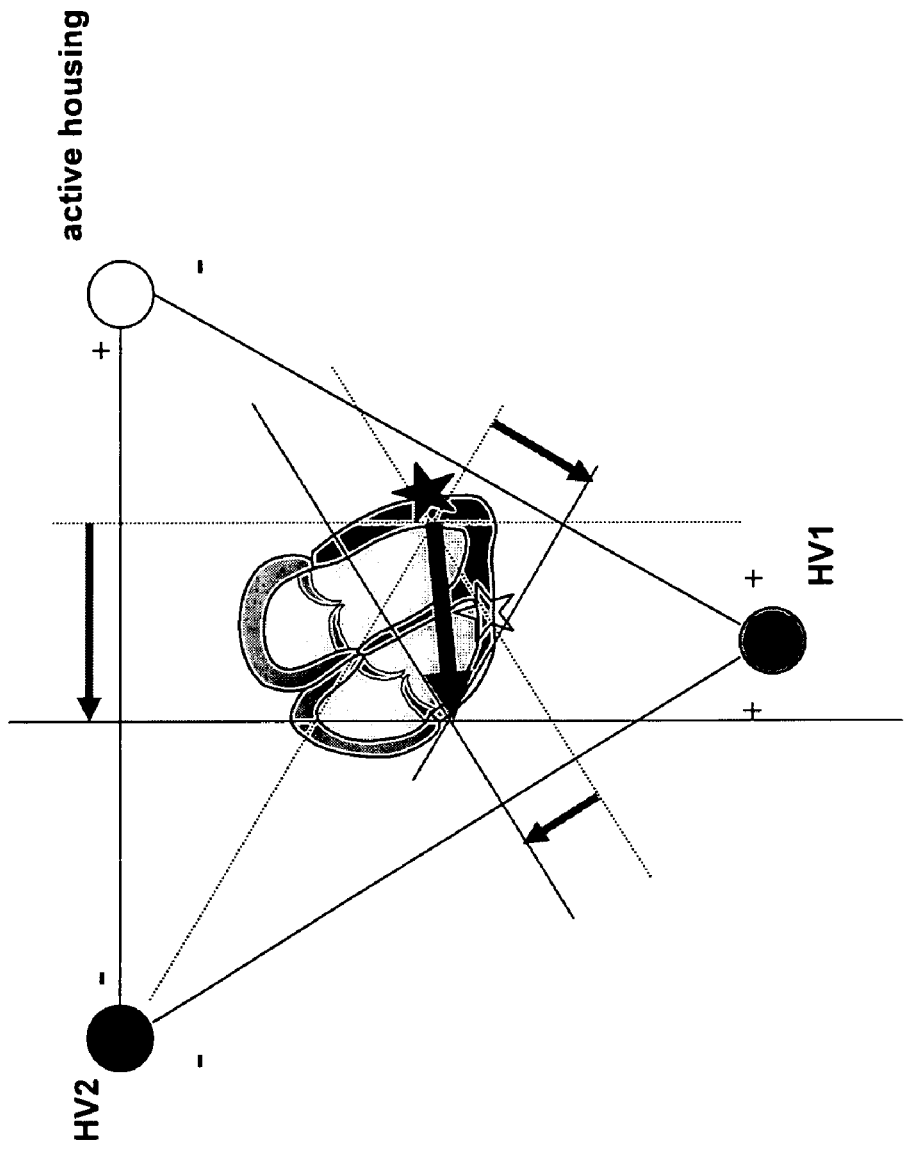
FIG. 20: shows a sketch, similar to FIG. 6, but here for the case in which the stimulation is only successful in the left ventricle.

In FIG. 16 and following FIGS. 18 and 20, a solid five-pointed star identifies the location of an effective stimulation, while an empty (white) five-pointed star identifies the location of an ineffective stimulation.

Figure 19:
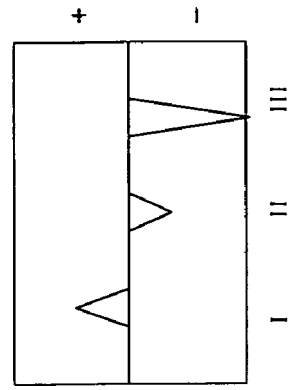
FIG. 19: shows a compact illustration of the amplitudes, similar to FIG. 7, for the case of a right-ventricular stimulation success and a left-ventricular capture loss, as shown in FIG. 12.

FIG. 18 and the associated compact illustration of the maximum amplitudes of the differential signals show how an ineffective stimulation in the left ventricle acts on the direction of the excitation propagation (see FIG. 18) and the absolute values and the signs of the maximum amplitudes (see FIG. 19).

Figure 21:
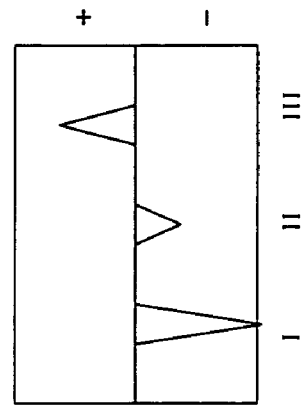
FIG. 21: shows the amplitudes of the electrocardiograms on which the sketch in FIG. 14 is based in a compact illustration, similar to FIG. 7.

Correspondingly, FIGS. 20 and 21 represent the case of the ineffective right-ventricular stimulation.

It is notable that the characteristic angle changes of the summation vector as a result of the altered propagation direction may already be inferred from the signs of the individual maximum amplitudes.

A special advantage of the stimulation success control on the basis of the analysis of the maximum amplitudes of the differential signals presented here is that this analysis and thus the establishment of a stimulation success may occur without the strength of the stimulation pulses having to be changed for this purpose.

In typical stimulation devices having automatic stimulation strength adaptation, the strength of the stimulation pulses is reduced step-by-step until a lack of stimulation success is established. In the stimulation success control on the basis of the analysis of the maximum amplitudes of the differential signals, the further advantage results that the shock electrodes and not the stimulation electrodes may be used for the stimulation success control. Moreover, the detection of the stimulation success on the basis of the analysis of the maximum amplitudes is independent of set pacemaker parameters.

As may be seen from FIGS. 18 and 20, the signal processing unit may be implemented for stimulation success control so that it responds to a sudden change of the excitation propagation direction. Depending on whether this sudden direction change is an angle change to the left or right, it may be seen by the signal processing unit in which of the chambers the capture loss has occurred.

If a capture loss is established, the stimulation device is preferably implemented to increase the stimulation strength for the particular chamber step-by-step (for example, in steps of 0.1 V) until a new excitation propagation direction which is characteristic for stimulation successful on both sides results again.

Figure 22:
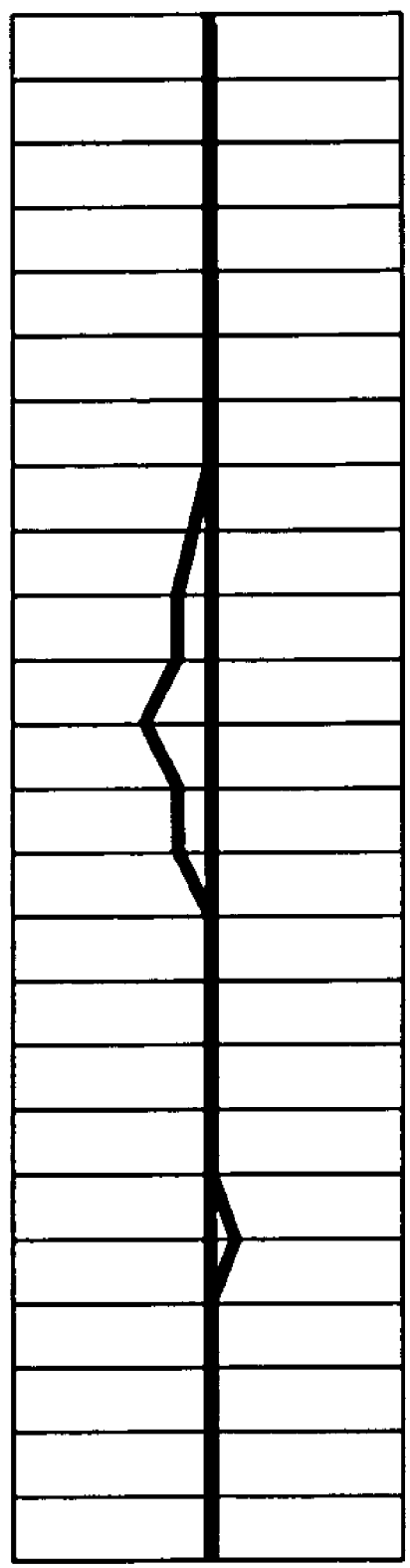
FIG. 22: shows a report about right-side or left-side capture losses, to be prepared here with the aid of a triple-chamber ICD according to the present invention and transmitted telemetrically to a home-monitoring center.

As FIG. 22 shows, the information about right-ventricular or left-ventricular capture losses obtained in the way described may be summarized into a report, which may be transmitted telemetrically from the implanted stimulation devices, for example, to a home monitoring center. FIG. 18 shows the possible appearance of such a report. In order to produce such a report, the signal processing unit is implemented to count events of lacking right-ventricular or left-ventricular stimulation success day by day and to transmit these numbers telemetrically to a home monitoring center.

Figure 23:
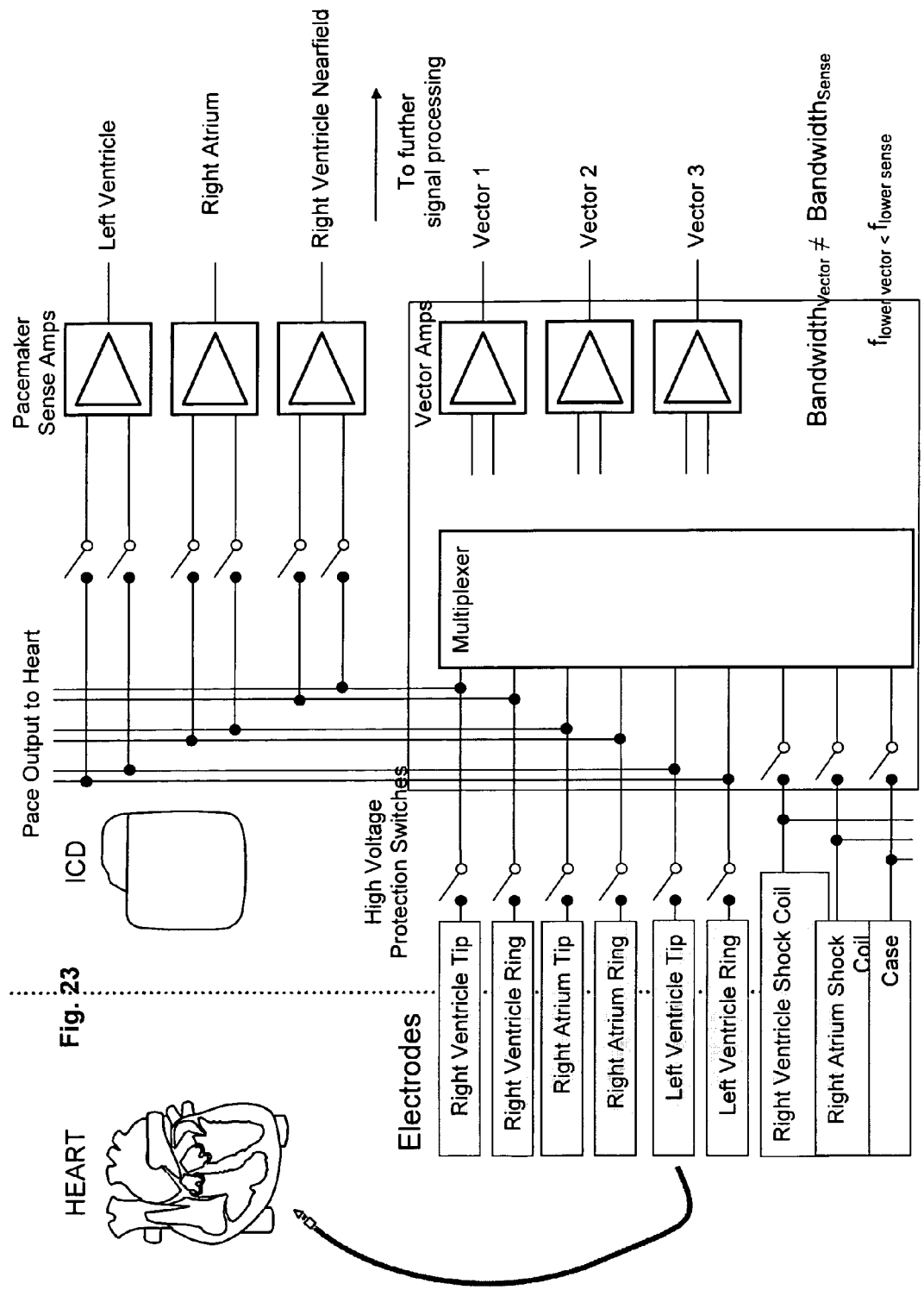
FIG. 23: shows a schematic illustration of the input channels of an ICD according to the present invention.
Figure 25:
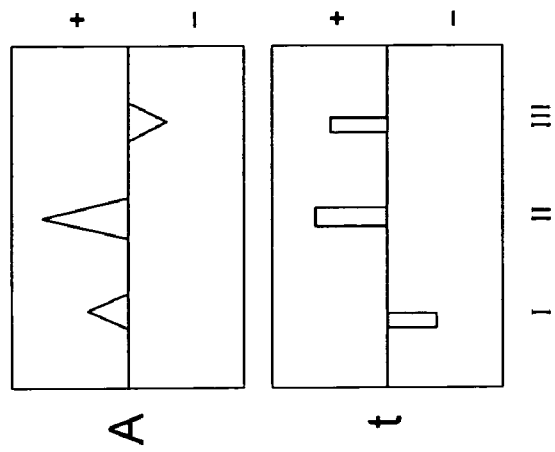
FIG. 25: shows a compact illustration of the maximum amplitudes of the far field signals shown in FIG. 24 and, in addition, a compact illustration of the time offset between the particular instant of the occurrence of a maximum amplitude in relation to the instant of the trigger signal.

FIG. 23 shows a schematic illustration of the input channels of an ICD according to embodiments of the invention having a Multiplexer that allows for the selection of various Electrodes (RV Tip, RV Ring, etc., as shown) as inputs for Vectors (Vector 1, Vector 2, Vector 3 as shown) for further signal processing. As one skilled in the art will appreciate, the Multiplexer allows for selection of desired electrodes inputs for further signal processing at the output side of the Multiplexer.

Figure 24:
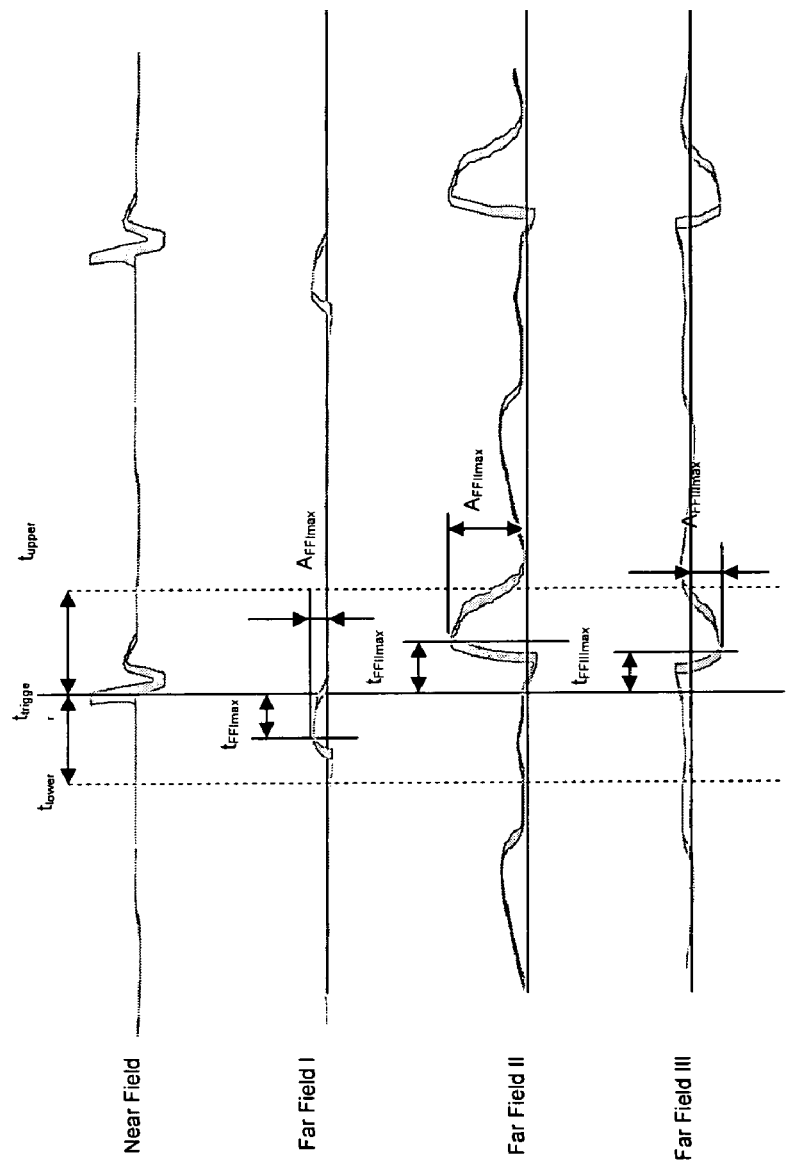
FIG. 24: shows the input signals of a near field channel as the trigger channel and of three far field channels, a time window being determined by a trigger signal derived from the near field channel, which begins chronologically before the trigger signal and ends after the trigger signal; this embodiment variation requires a loop recorder.

FIGS. 24 through 27 show how the input signals of three far field channels within a time window, which is related to an instant $t_{trigger}$, which is derived from the input signal of a near field channel, are analyzed. In FIG. 24, the time window begins at an instant $t_{lower}$, which is before the instant $t_{trigger}$, and ends with an instant $t_{upper}$, which is after the instant $t_{trigger}$. The embodiment variation shown in FIG. 24 thus requires a loop recorder for recording the total of four input signals. In the embodiment variation shown in FIGS. 26 and 27, the time window begins at an instant $t_{lower}$, which is after the instant $t_{trigger}$, so that no loop recorder is required for the embodiment variation shown in FIGS. 26 and 27.

Figures 26, 27:
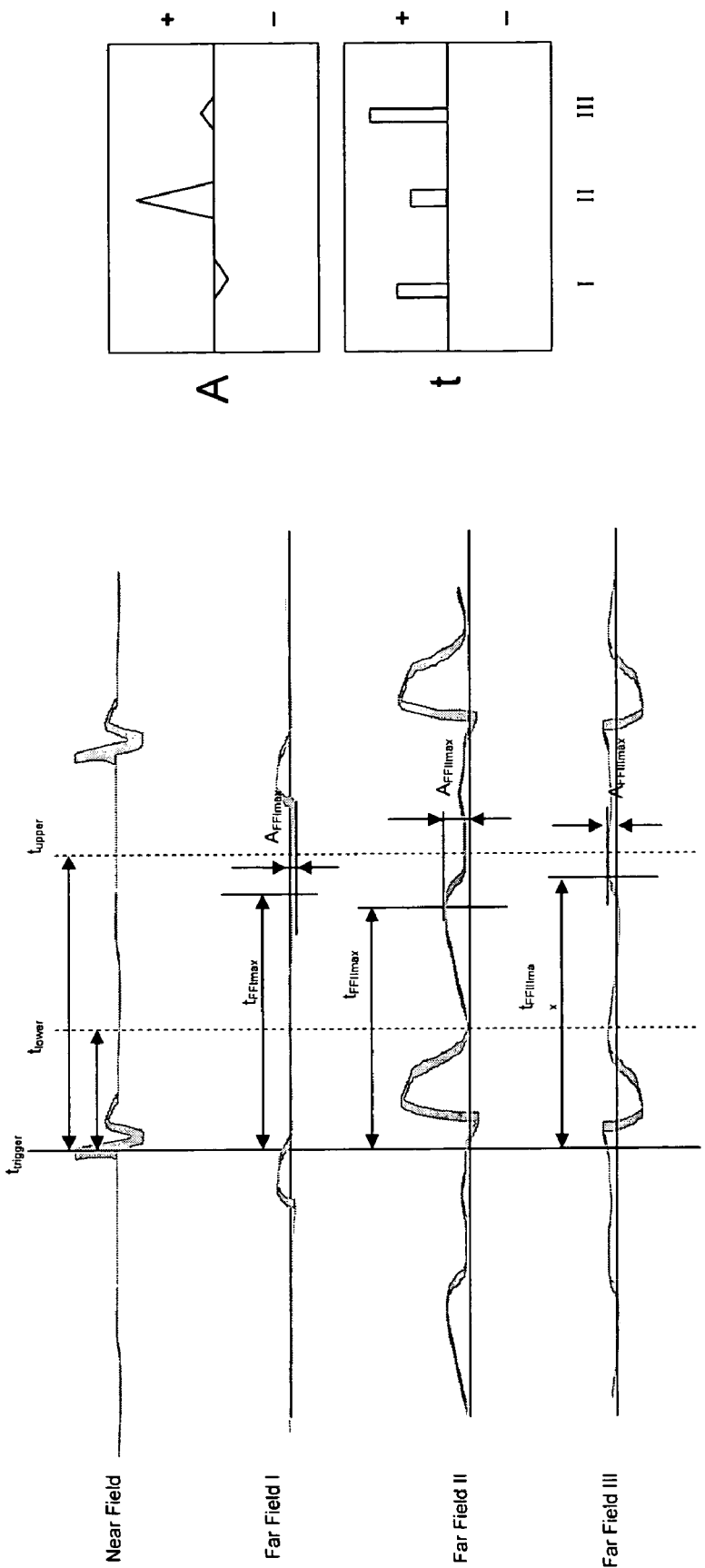
FIG. 26: shows the input signals of a near field channel as a trigger signal and of three far field channels, a time window being determined by a trigger signal derived from the near field channel which begins chronologically after the trigger signal and ends after the trigger signal.
FIG. 27: shows a compact illustration of the maximum amplitudes of the far field signals shown in FIG. 26 and, in addition, a compact illustration of the time offset between the particular instant of the occurrence of a maximum amplitude in relation to the instant of the trigger signal.

It is to be noted that in the exemplary embodiment shown in FIGS. 24 through 27, only the maximum amplitudes ($A_{FFmax}$) of the particular far field signals within the time window, i.e., between the instants $t_{lower}$ and $t_{upper}$, are always detected. FIG. 26 shows that these are not necessarily the absolute amplitude maxima of the particular far field signals within a particular cardiac cycle.

In addition, FIGS. 24 through 27 show that besides the maximum amplitude values $A_{FFmax}$ within the time window, the instants ($t_{FFmax}$) of the occurrence of these maximum amplitudes are also detected and analyzed. These instants may also be represented as a 3-tuple—similar to the maximum amplitude values—which is graphically shown in compact form in FIGS. 25 and 27.

What is claimed is:

1. An implantable electrostimulation device comprising:
at least one electrode or one terminal for an electrode;
at least three input channels, which are each connected to said at least one electrode or one terminal for an electrode, wherein said at least three input channels are configured to detect at least three different electrical potentials that accompany an excitation of cardiac tissue in a heart, wherein said at least three input channels form at least three sensing channels;
memory configured to store data;
a signal processing unit connected to said at least three input channels wherein said signal processing unit is configured to
analyze a time curve of potentials detected via said at least three sensing channels as three input signals in chronological relation to a periodically repeating trigger signal, which triggers a time window;
detect predefined signal features for each of said three input signals within said time window triggered by said periodically repeating trigger signal;
determine either a maximum amplitude value for each of said three differential signals or a time offset in said time window of said maximum amplitude value for each of said three differential signals;
calculate one summation vector per cardiac cycle for said three input signals within said time window triggered by said periodically repeating trigger signal using either said maximum amplitude value for each of said three differential signals or said time offset in said time window of said maximum amplitude value for each of said three differential signals;
store said one summation vector per said cardiac cycle in said memory; and
compare said one summation vector to
a corresponding summation vector of a preceding time window,
determine a change in angle between said summation vector and said summation vector of said preceding time window.

2. The implantable electrostimulation device according to claim 1 wherein said signal processing unit is further configured to
compare a detected current signal feature of an input signal in regard to an instant of an occurrence of a shape feature in said time window to an instant of an occurrence of a corresponding shape feature in another input signal or in a preceding time window.

3. The implantable electrostimulation device according to claim 1 wherein said signal processing unit is further configured to
detect an instant of an occurrence of an amplitude maximum in said time window as a signal feature.

4. The implantable electrostimulation device according to claim 1 wherein said signal processing unit is further configured to
detect an instant of an occurrence of said signal feature in relation to a duration of said time window.

5. The implantable electrostimulation device according to claim 1 wherein said signal processing unit is further configured to
derive a trigger signal from one of said three input signals in such a way that said trigger signal is triggered by a signal feature of said one of said three input signals.

6. The implantable electrostimulation device according to claim 5 wherein said signal processing unit is further configured to
derive said trigger signal from said input signal which represents a near field potential.

7. The implantable electrostimulation device according to claim 5 wherein said implantable electrostimulation device has
a fourth input channel as a fourth sensing channel, which is connected to another at least one electrode or one terminal for an electrode, wherein said fourth input channel is configured to detect a near field of an electrical potential that accompanies an excitation of said cardiac tissue in said heart, and
wherein said signal processing unit is further configured to derive said trigger signal from an input signal of said fourth sensing channel.

8. The implantable electrostimulation device according to claim 7 wherein
said at least three sensing channels are far field channels and are each connected to an electrode or a terminal for an electrode, wherein said far field channels are configured to detect a far field of an electrical potential that accompanies said excitation of said cardiac tissue in an operating state of said implantable electrostimulation device, and
wherein said fourth sensing channel is a near field channel, which is connected to an electrode or to a terminal for an electrode, wherein said fourth sensing channel is configured to detect said near field of said electrical potential that accompanies said excitation of said cardiac tissue in said operating state of said implantable electrostimulation device.

9. The implantable electrostimulation device according to claim 6 wherein said input signal that represents said near field potential is detected via a near field channel, to which at least one bipolar, right-ventricular electrode line is connected or is to be connected, which has a ventricular ring electrode and a ventricular tip electrode, via which said near field potential is detected.

10. The implantable electrostimulation device according to claim 1 wherein said signal processing unit comprises a loop recorder configured to record input signal sections and wherein said signal processing unit is further configured to
perform detection of said predefined signal features in said time window, which begins before an occurrence of a trigger signal, triggered by said trigger signal.

11. The implantable electrostimulation device according to claim 1 wherein said signal processing unit has a signal template memory and is further configured to
detect said predefined signal features on a basis of a comparison of a particular input signal to a stored signal template.

12. The implantable electrostimulation device according to claim 1 wherein said at least three input channels are far field channels, which are each connected to an electrode or to a terminal for an electrode, wherein said far field channels are configured to detect a far field of an electrical potential that accompanies said excitation of said cardiac tissue in an operating state of said implantable electrostimulation device, so that an input signal that represents a particular far field is applied to said at least three input channels.

13. The implantable electrostimulation device according to claim 12 wherein said electrostimulation device is configured as an implantable cardioverter/defibrillator, and, of said far field channels, a first is connected to an electrode formed by a housing of said implantable cardioverter/defibrillator and a terminal for a proximal defibrillation electrode or atrial shock electrode, a second input channel is connected to an electrode formed by said housing of said implantable cardioverter/defibrillator and a terminal for a distal defibrillation electrode or ventricular shock electrode, and a third input channel is connected to a terminal for a distal defibrillation electrode and said terminal for a proximal defibrillation electrode.

14. The implantable electrostimulation device according to claim 12 wherein said signal processing unit is further configured to
analyze differential signals detected via said three far field channels in regard to absolute value and sign of their maximum amplitude value in comparison to one another.

15. The implantable electrostimulation device according to claim 12 wherein said signal processing unit is further configured to
derive an electrocardiogram from each of said differential signals received via each two far field channels.

16. The implantable electrostimulation device according to claim 15 wherein said signal processing unit is further configured to
derive three electrocardiograms from those differential signals which originate from three different input channels, respectively from pairs of input channels selected from said three different input channels.

17. The implantable electrostimulation device according to claim 16 wherein said signal processing unit is further configured to
determine a particular maximum deflection in an area of a QRS complex as a signal feature for each electrocardiogram.

18. The implantable electrostimulation device according to claim 16 wherein said electrostimulation device has a memory, in which an angle value is stored for each of said differential signals or said electrocardiograms, wherein said signal processing unit is connected to said memory and wherein said signal processing unit is further configured to analyze said particular maximum amplitude of said particular differential signal or an amplitude of said particular electrocardiogram together with an associated angle value.

19. The implantable electrostimulation device according to claim 18 wherein said signal processing unit is further configured to
analyze maximum amplitudes of said differential signals or maximum deflections of said electrocardiograms as vector components of said summation vector and to
determine and analyze a direction of said summation vector.

20. The implantable electrostimulation device according to claim 19 wherein said signal processing unit is further configured to
derive said summation vector as an Einthoven summation vector from said maximum deflections of three different electrocardiograms at an instant of an R wave of a particular cardiac cycle.

21. The implantable electrostimulation device according to claim 18 wherein said signal processing unit is further configured to
determine said direction of said summation vector anew for every cardiac cycle.

22. The implantable electrostimulation device according to claim 21 wherein said signal processing unit works together with said memory for at least said direction of said summation vector for at least one preceding cardiac cycle and is further configured to
detect a change of said direction of said summation vector beyond a predefined minimum amount.

23. The implantable electrostimulation device according to claim 22 wherein said signal processing unit is further configured to
detect a change of said direction of said summation vector for more than one cardiac cycle.

24. The implantable electrostimulation device according to claim 22 wherein said signal processing unit is further configured to
analyze an input signal that characterizes a near field in regard to signal peaks that each characterize a ventricular contraction.

25. The implantable electrostimulation device according to claim 24 wherein said signal processing unit is further configured to
analyze a chronological interval of said signal peaks in regard to a heart rate or an RR interval.

26. The implantable electrostimulation device according to claim 24 wherein said signal processing unit is further configured to
derive a marker signal from said signal peaks.

27. The implantable electrostimulation device according to claim 26 wherein said signal processing unit is further configured to
determine an amplitude of a differential signal or said electrocardiogram for each cardiac cycle at an instant of a particular marker signal and to
analyze amplitudes thus obtained as absolute values of components of said summation vector to determine a direction of said summation vector.

28. The implantable electrostimulation device according to claim 25 wherein said electrostimulation device has a tachycardia classification unit, which is connected to said signal processing unit and is configured to classify a ventricular tachycardia through analysis of RR intervals or RR rate and said absolute value and sign of said maximum amplitude values of said differential signals or said absolute value and sign of said amplitudes of said electrocardiograms.

29. The implantable electrostimulation device according to claim 25 wherein said electrostimulation device has a tachycardia classification unit, which is connected to said signal processing unit and is configured to classify a ventricular tachycardia through analysis of a direction of said summation vector and RR intervals or RR rate.

30. The implantable electrostimulation device according to claim 1 wherein said electrostimulation device has a stimulation success detection unit, which is connected to said signal processing unit and is configured to
detect a stimulated contraction of a heart chamber on a basis of said absolute value and sign of said maximum amplitude values of said differential signals or said absolute value and sign of said amplitudes of said electrocardiograms and
assign said stimulated contraction to said heart chamber.

31. The implantable electrostimulation device according to claim 19 wherein said electrostimulation device has a stimulation success detection unit, which is connected to said signal processing unit and is configured to
detect a stimulated contraction of a heart chamber through analysis of said direction of said summation vector and assign said stimulated contraction to said heart chamber.

* * * * *